(12) United States Patent
Posnack et al.

(10) Patent No.: US 11,701,548 B2
(45) Date of Patent: Jul. 18, 2023

(54) COMPUTER-IMPLEMENTED QUESTIONNAIRE FOR ORTHOPEDIC TREATMENT

(71) Applicant: ROM TECHNOLOGIES, INC., Las Vegas, NV (US)

(72) Inventors: Daniel Posnack, Fort Lauderdale, FL (US); Peter Arn, Roxbury, CT (US); S. Adam Hacking, Nashua, NH (US); Micheal Mueller, Oil City, PA (US); Joseph Guaneri, Merrick, NY (US); Jonathan Greene, Denver, CO (US)

(73) Assignee: Rom Technologies, Inc., Brookfield, CT (US)

( * ) Notice: Subject to any disclaimer, the term of this patent is extended or adjusted under 35 U.S.C. 154(b) by 44 days.

(21) Appl. No.: 17/021,899

(22) Filed: Sep. 15, 2020

(65) Prior Publication Data
US 2021/0101051 A1    Apr. 8, 2021

Related U.S. Application Data

(60) Provisional application No. 62/911,638, filed on Oct. 7, 2019.

(51) Int. Cl.
*G16H 10/20*    (2018.01)
*G16H 10/60*    (2018.01)
(Continued)

(52) U.S. Cl.
CPC .... *A63B 24/0075* (2013.01); *A63B 21/00178* (2013.01); *A63B 22/0694* (2013.01);
(Continued)

(58) Field of Classification Search
None
See application file for complete search history.

(56) References Cited

U.S. PATENT DOCUMENTS

| 4,822,032 A | 4/1989 | Whitmore et al. |
| 4,860,763 A | 8/1989 | Schminke |

(Continued)

FOREIGN PATENT DOCUMENTS

| CA | 2698078 A1 | 3/2010 |
| CN | 112603295 A | 2/2003 |

(Continued)

OTHER PUBLICATIONS

I. c. Jeong and J. Finkelstein, "Computer-assisted upper extremity training using interactive biking exercise (iBikE) platform," 2012 Annual International Conference of the IEEE Engineering in Medicine and Biology Society, San Diego, CA, USA, 2012, pp. 6095-6099, doi: 10.1109/EMBC.2012.6347384. (Year: 2012).*

(Continued)

*Primary Examiner* — Rachelle L Reichert
(74) *Attorney, Agent, or Firm* — Dickinson Wright PLLC; Stephen A. Mason; Jonathan H. Harder

(57) ABSTRACT

A system for physical rehabilitation comprises a clinician interface including a patient profile display presenting data regarding performance of a regimen for a body part. A patient interface presents instructions and status information regarding the performance of the regimen. The patient interface further presents a questionnaire soliciting responses to questions pertaining to current and past physical conditions of the patient. Selected responses to the questions cause the system to take actions, including preventing operation of a treatment apparatus by the patient, and/or transmitting an alert message to a clinician. The alert message may be transmitted within the clinician interface and/or as a real-time message outside of the clinician interface. A questionnaire is presented to the patient in response to occurrence of a triggering event pertaining to the patient's use of the treatment apparatus.

24 Claims, 19 Drawing Sheets

(51) Int. Cl.
*G16H 70/20* (2018.01)
*G16H 20/30* (2018.01)
*A63B 24/00* (2006.01)
*A63B 22/06* (2006.01)
*A63B 71/06* (2006.01)
*A63B 21/00* (2006.01)
*A63B 22/00* (2006.01)

(52) U.S. Cl.
CPC ...... *A63B 24/0062* (2013.01); *A63B 71/0622* (2013.01); *G16H 10/20* (2018.01); *G16H 10/60* (2018.01); *G16H 20/30* (2018.01); *G16H 70/20* (2018.01); *A63B 2022/0094* (2013.01); *A63B 2071/0675* (2013.01); *A63B 2220/51* (2013.01)

(56) References Cited

U.S. PATENT DOCUMENTS

| | | |
|---|---|---|
| 4,932,650 A | 6/1990 | Bingham et al. |
| 5,137,501 A | 8/1992 | Mertesdorf |
| 5,240,417 A | 8/1993 | Smithson et al. |
| 5,256,117 A | 10/1993 | Potts et al. |
| 5,284,131 A | 2/1994 | Gray |
| 5,429,140 A | 7/1995 | Burdea et al. |
| 5,738,636 A | 4/1998 | Saringer et al. |
| 6,110,130 A | 8/2000 | Kramer |
| 6,182,029 B1 | 1/2001 | Friedman |
| 6,267,735 B1 | 7/2001 | Blanchard et al. |
| 6,273,863 B1 | 8/2001 | Avni et al. |
| 6,413,190 B1 | 7/2002 | Wood et al. |
| 6,436,058 B1 | 8/2002 | Krahner et al. |
| 6,491,649 B1 | 12/2002 | Ombrellaro |
| 6,535,861 B1 | 3/2003 | OConnor et al. |
| 6,602,191 B2 | 8/2003 | Quy |
| 6,626,805 B1 | 9/2003 | Lightbody |
| 6,652,425 B1 | 11/2003 | Martin et al. |
| 6,890,312 B1 | 5/2005 | Priester et al. |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,209,886 B2 | 4/2007 | Kimmel |
| 7,226,394 B2 | 6/2007 | Johnson |
| RE39,904 E | 10/2007 | Lee |
| 7,507,188 B2 | 3/2009 | Nurre |
| 7,594,879 B2 | 9/2009 | Johnson |
| 7,778,851 B2 | 8/2010 | Schoenberg et al. |
| 7,809,601 B2 | 10/2010 | Shaya et al. |
| 7,833,135 B2 | 11/2010 | Radow et al. |
| 7,837,472 B1 | 11/2010 | Elsmore et al. |
| 7,955,219 B2 | 6/2011 | Birrell et al. |
| 7,974,689 B2 | 7/2011 | Volpe et al. |
| 7,988,599 B2 | 8/2011 | Ainsworth et al. |
| 8,079,937 B2 | 12/2011 | Bedell et al. |
| 8,287,434 B2 | 10/2012 | Zavadsky et al. |
| 8,419,593 B2 | 4/2013 | Ainsworth et al. |
| 8,465,398 B2 | 6/2013 | Lee et al. |
| 8,506,458 B2 | 8/2013 | Dugan |
| 8,540,515 B2 | 9/2013 | Williams et al. |
| 8,540,516 B2 | 9/2013 | Williams et al. |
| 8,556,778 B1 | 10/2013 | Dugan |
| 8,613,689 B2 | 12/2013 | Dyer et al. |
| 8,672,812 B2 | 3/2014 | Dugan |
| 8,751,264 B2 | 6/2014 | Beraja et al. |
| 8,784,273 B2 | 7/2014 | Dugan |
| 8,818,496 B2 | 8/2014 | Dziubinski et al. |
| 8,823,448 B1 | 9/2014 | Shen |
| 8,864,628 B2 | 10/2014 | Boyette et al. |
| 8,979,711 B2 | 3/2015 | Dugan |
| 9,167,281 B2 | 10/2015 | Petrov et al. |
| 9,248,071 B1 | 2/2016 | Benda et al. |
| 9,272,185 B2 | 3/2016 | Dugan |
| 9,283,434 B1 | 3/2016 | Wu |
| 9,311,789 B1 | 4/2016 | Gwin |
| 9,312,907 B2 | 4/2016 | Auchinleck et al. |
| 9,367,668 B2 | 6/2016 | Flynt et al. |
| 9,409,054 B2 | 8/2016 | Dugan |
| 9,443,205 B2 | 9/2016 | Wall |
| 9,481,428 B2 | 11/2016 | Gros et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,717,947 B2 | 8/2017 | Lin |
| 9,737,761 B1 | 8/2017 | Govindarajan |
| 9,782,621 B2 | 10/2017 | Chiang et al. |
| 9,802,076 B2 | 10/2017 | Murray et al. |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 10,074,148 B2 | 9/2018 | Cashman et al. |
| 10,130,298 B2 | 11/2018 | Mokaya et al. |
| 10,130,311 B1 | 11/2018 | De Sapio et al. |
| 10,155,134 B2 | 12/2018 | Dugan |
| 10,159,872 B2 | 12/2018 | Sasaki et al. |
| 10,173,094 B2 | 1/2019 | Gomberg |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,226,663 B2 | 3/2019 | Gomberg et al. |
| 10,325,070 B2 | 6/2019 | Beale et al. |
| 10,327,697 B1 | 6/2019 | Stein et al. |
| 10,424,033 B2 | 9/2019 | Romeo |
| 10,430,552 B2 | 10/2019 | Mihai |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| 10,792,495 B2 | 10/2020 | Izvorski et al. |
| 10,874,905 B2 | 12/2020 | Belson et al. |
| D907,143 S | 1/2021 | Ach et al. |
| 10,918,332 B2 | 2/2021 | Belson et al. |
| 10,931,643 B1 | 2/2021 | Neumann |
| 11,000,735 B2 | 5/2021 | Orady et al. |
| 11,045,709 B2 | 6/2021 | Putnam |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| D939,644 S | 12/2021 | Ach et al. |
| D940,797 S | 1/2022 | Ach et al. |
| 11,229,727 B2 | 1/2022 | Tatonetti |
| 11,270,795 B2 | 3/2022 | Mason et al. |
| 11,272,879 B2 | 3/2022 | Wiedenhoefer et al. |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,348,683 B2 | 5/2022 | Guaneri et al. |
| 11,404,150 B2 | 8/2022 | Guaneri et al. |
| 11,410,768 B2 | 8/2022 | Mason et al. |
| 11,508,482 B2 | 11/2022 | Mason et al. |

(56) References Cited

U.S. PATENT DOCUMENTS

| | | |
|---|---|---|
| 11,515,021 B2 | 11/2022 | Mason |
| 11,515,028 B2 | 11/2022 | Mason |
| 11,541,274 B2 | 1/2023 | Hacking |
| 2002/0072452 A1 | 6/2002 | Torkelson |
| 2002/0160883 A1 | 10/2002 | Dugan |
| 2003/0036683 A1 | 2/2003 | Kehr et al. |
| 2003/0064863 A1 | 4/2003 | Chen |
| 2003/0181832 A1 | 9/2003 | Carnahan et al. |
| 2004/0102931 A1 | 5/2004 | Ellis et al. |
| 2004/0147969 A1 | 7/2004 | Mann et al. |
| 2005/0043153 A1 | 2/2005 | Krietzman |
| 2006/0046905 A1 | 3/2006 | Doody, Jr. et al. |
| 2006/0064329 A1 | 3/2006 | Abolfathi et al. |
| 2006/0199700 A1 | 9/2006 | LaStayo et al. |
| 2007/0042868 A1 | 2/2007 | Fisher et al. |
| 2007/0137307 A1 | 6/2007 | Gruben et al. |
| 2007/0173392 A1 | 7/2007 | Stanford |
| 2007/0287597 A1 | 12/2007 | Cameron |
| 2008/0021834 A1 | 1/2008 | Holla et al. |
| 2008/0096726 A1 | 4/2008 | Riley et al. |
| 2008/0153592 A1 | 6/2008 | James-Herbert |
| 2008/0300914 A1 | 12/2008 | Karkanias et al. |
| 2009/0011907 A1 | 1/2009 | Radow et al. |
| 2009/0058635 A1 | 3/2009 | LaLonde et al. |
| 2009/0070138 A1 | 3/2009 | Langheier et al. |
| 2009/0270227 A1 | 10/2009 | Ashby et al. |
| 2010/0048358 A1 | 2/2010 | Tchao et al. |
| 2010/0121160 A1 | 5/2010 | Stark et al. |
| 2010/0173747 A1 | 7/2010 | Chen et al. |
| 2010/0248899 A1 | 9/2010 | Bedell et al. |
| 2010/0268304 A1 | 10/2010 | Matos |
| 2010/0298102 A1 | 11/2010 | Bosecker et al. |
| 2011/0047108 A1 | 2/2011 | Chakrabarty et al. |
| 2011/0172059 A1 | 7/2011 | Watterson et al. |
| 2011/0195819 A1 | 8/2011 | Shaw et al. |
| 2011/0218814 A1 | 9/2011 | Coats |
| 2011/0275483 A1 | 11/2011 | Dugan |
| 2012/0065987 A1 | 3/2012 | Farooq et al. |
| 2012/0116258 A1 | 5/2012 | Lee |
| 2012/0183939 A1 | 7/2012 | Aragones et al. |
| 2012/0190502 A1 | 7/2012 | Paulus et al. |
| 2012/0232438 A1 | 9/2012 | Cataldi et al. |
| 2012/0295240 A1 | 11/2012 | Walker et al. |
| 2012/0310667 A1 | 12/2012 | Altman et al. |
| 2013/0123667 A1 | 5/2013 | Komatireddy et al. |
| 2013/0137550 A1 | 5/2013 | Skinner et al. |
| 2013/0178334 A1 | 7/2013 | Brammer |
| 2013/0296987 A1 | 11/2013 | Rogers et al. |
| 2013/0318027 A1 | 11/2013 | Almogy et al. |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0113768 A1* | 4/2014 | Lin .................. A63B 71/0619 482/5 |
| 2014/0155129 A1 | 6/2014 | Dugan |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0207486 A1 | 7/2014 | Carty et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0309083 A1 | 10/2014 | Dugan |
| 2014/0322686 A1 | 10/2014 | Kang |
| 2015/0045700 A1 | 2/2015 | Cavanagh et al. |
| 2015/0088544 A1 | 3/2015 | Goldberg |
| 2015/0094192 A1 | 4/2015 | Skwortsow et al. |
| 2015/0151162 A1 | 6/2015 | Dugan |
| 2015/0158549 A1 | 6/2015 | Gros et al. |
| 2015/0161331 A1 | 6/2015 | Oleynik |
| 2015/0290061 A1 | 10/2015 | Stafford et al. |
| 2015/0339442 A1 | 11/2015 | Oleynik |
| 2015/0341812 A1 | 11/2015 | Dion et al. |
| 2015/0360069 A1 | 12/2015 | Marti et al. |
| 2015/0379232 A1* | 12/2015 | Mainwaring .......... G16H 50/70 705/2 |
| 2016/0007885 A1 | 1/2016 | Basta et al. |
| 2016/0117471 A1 | 4/2016 | Belt et al. |
| 2016/0140319 A1 | 5/2016 | Stark et al. |
| 2016/0151670 A1 | 6/2016 | Dugan |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2016/0361597 A1 | 12/2016 | Cole et al. |
| 2017/0004260 A1 | 1/2017 | Moturu et al. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0106242 A1 | 4/2017 | Dugan |
| 2017/0128769 A1* | 5/2017 | Long ...................... A63B 22/02 |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147789 A1 | 5/2017 | Wiedenhoefer et al. |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0209766 A1 | 7/2017 | Riley et al. |
| 2017/0243028 A1 | 8/2017 | LaFever et al. |
| 2017/0265800 A1 | 9/2017 | Auchinleck et al. |
| 2017/0266501 A1 | 9/2017 | Sanders et al. |
| 2017/0278209 A1 | 9/2017 | Olsen et al. |
| 2017/0282015 A1 | 10/2017 | Wicks et al. |
| 2017/0300654 A1 | 10/2017 | Stein et al. |
| 2017/0312614 A1 | 11/2017 | Tran et al. |
| 2017/0329917 A1 | 11/2017 | McRaith et al. |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0036593 A1 | 2/2018 | Ridgel et al. |
| 2018/0052962 A1 | 2/2018 | Van Der Koijk et al. |
| 2018/0056104 A1 | 3/2018 | Cromie et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0096111 A1 | 4/2018 | Wells et al. |
| 2018/0102190 A1 | 4/2018 | Hogue et al. |
| 2018/0116741 A1 | 5/2018 | Garcia Kilroy et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0240552 A1 | 8/2018 | Tuyl et al. |
| 2018/0253991 A1 | 9/2018 | Tang et al. |
| 2018/0256079 A1 | 9/2018 | Yang et al. |
| 2018/0263530 A1 | 9/2018 | Jung |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296157 A1 | 10/2018 | Bleich et al. |
| 2018/0326243 A1 | 11/2018 | Badi et al. |
| 2018/0330058 A1 | 11/2018 | Bates |
| 2018/0330824 A1 | 11/2018 | Athey et al. |
| 2018/0360340 A1 | 12/2018 | Rehse et al. |

(56) References Cited

U.S. PATENT DOCUMENTS

| | | |
|---|---|---|
| 2018/0373844 A1 | 12/2018 | Ferrandez-Escamez et al. |
| 2019/0019578 A1* | 1/2019 | Vaccaro ............... A61B 5/7275 |
| 2019/0030415 A1 | 1/2019 | Volpe, Jr. |
| 2019/0031284 A1 | 1/2019 | Fuchs |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0088356 A1 | 3/2019 | Oliver et al. |
| 2019/0111299 A1 | 4/2019 | Radcliffe et al. |
| 2019/0115097 A1 | 4/2019 | Macoviak et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0304584 A1 | 10/2019 | Savolainen |
| 2019/0366146 A1 | 12/2019 | Tong et al. |
| 2019/0388728 A1 | 12/2019 | Wang et al. |
| 2020/0066390 A1 | 2/2020 | Svendrys et al. |
| 2020/0085300 A1* | 3/2020 | Kwatra .................. G16H 20/00 |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0334972 A1 | 10/2020 | Gopalakrishnan |
| 2020/0357299 A1 | 11/2020 | Patel et al. |
| 2020/0395112 A1 | 12/2020 | Ronner |
| 2020/0401224 A1 | 12/2020 | Cotton |
| 2021/0035674 A1 | 2/2021 | Volosin et al. |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0098129 A1 | 4/2021 | Neumann |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0202090 A1 | 7/2021 | ODonovan et al. |
| 2021/0202103 A1 | 7/2021 | Bostic et al. |
| 2021/0244998 A1 | 8/2021 | Hacking et al. |
| 2021/0245003 A1 | 8/2021 | Turner |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0407670 A1 | 12/2021 | Mason et al. |
| 2021/0407681 A1 | 12/2021 | Mason et al. |
| 2022/0015838 A1 | 1/2022 | Posnack et al. |
| 2022/0047921 A1 | 2/2022 | Bissonnette et al. |
| 2022/0079690 A1 | 3/2022 | Mason et al. |
| 2022/0080256 A1 | 3/2022 | Arn et al. |
| 2022/0105384 A1 | 4/2022 | Hacking et al. |
| 2022/0105385 A1 | 4/2022 | Hacking et al. |
| 2022/0115133 A1 | 4/2022 | Mason et al. |
| 2022/0126169 A1 | 4/2022 | Mason |
| 2022/0148725 A1 | 5/2022 | Mason et al. |
| 2022/0158916 A1 | 5/2022 | Mason et al. |
| 2022/0193491 A1 | 6/2022 | Mason et al. |
| 2022/0230729 A1 | 7/2022 | Mason et al. |
| 2022/0238222 A1 | 7/2022 | Neuberg |
| 2022/0238223 A1 | 7/2022 | Mason et al. |
| 2022/0262483 A1 | 8/2022 | Rosenberg et al. |
| 2022/0266094 A1 | 8/2022 | Mason et al. |
| 2022/0270738 A1 | 8/2022 | Mason et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0314075 A1 | 10/2022 | Mason et al. |
| 2022/0328181 A1 | 10/2022 | Mason et al. |
| 2022/0331663 A1 | 10/2022 | Mason |
| 2022/0339501 A1 | 10/2022 | Mason et al. |
| 2022/0384012 A1 | 12/2022 | Mason |
| 2022/0392591 A1 | 12/2022 | Guaneri et al. |
| 2022/0415469 A1 | 12/2022 | Mason |
| 2022/0415471 A1 | 12/2022 | Mason |
| 2023/0013530 A1 | 1/2023 | Mason |
| 2023/0014598 A1 | 1/2023 | Mason et al. |
| 2023/0048040 A1 | 2/2023 | Hacking et al. |
| 2023/0051751 A1 | 2/2023 | Hacking et al. |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |

FOREIGN PATENT DOCUMENTS

| | | |
|---|---|---|
| CN | 103488880 A | 1/2014 |
| CN | 104335211 A | 2/2015 |
| CN | 105683977 A | 6/2016 |
| CN | 105894088 A | 8/2016 |
| CN | 105930668 A | 9/2016 |
| CN | 106127646 A | 11/2016 |
| CN | 106510985 A | 3/2017 |
| CN | 107066819 A | 8/2017 |
| CN | 107430641 A | 12/2017 |
| CN | 107736982 A | 2/2018 |
| CN | 108078737 A | 5/2018 |
| CN | 208573971 U | 3/2019 |
| CN | 110148472 A | 8/2019 |
| CN | 110215188 A | 9/2019 |

(56) References Cited

FOREIGN PATENT DOCUMENTS

| | | |
|---|---|---|
| CN | 111105859 A | 5/2020 |
| CN | 111370088 A | 7/2020 |
| CN | 111790111 A | 10/2020 |
| CN | 112603295 A | 4/2021 |
| CN | 114632302 A | 6/2022 |
| DE | 102018202497 A1 | 8/2018 |
| DE | 102018211212 A1 | 1/2019 |
| DE | 102019108425 B3 | 8/2020 |
| EP | 0383137 A2 | 8/1990 |
| EP | 1391179 A1 | 2/2004 |
| EP | 3264303 A1 | 1/2018 |
| EP | 3323473 A1 | 5/2018 |
| EP | 3627514 A1 | 3/2020 |
| EP | 3671700 A1 | 6/2020 |
| EP | 3688537 A1 | 8/2020 |
| EP | 3731733 A1 | 11/2020 |
| GB | 2512431 A * | 10/2014 ............ A61M 1/14 |
| GB | 2512431 A | 10/2014 |
| JP | 2003225875 A | 8/2003 |
| JP | 2013515995 A | 5/2013 |
| JP | 3198173 U | 6/2015 |
| JP | 2019134909 A | 8/2019 |
| JP | 6573739 B1 | 9/2019 |
| JP | 6659831 B2 | 3/2020 |
| JP | 6710357 B1 | 6/2020 |
| JP | 6775757 B1 | 10/2020 |
| JP | 2021027917 A | 2/2021 |
| KR | 20020009724 A | 2/2002 |
| KR | 20020065253 A | 8/2002 |
| KR | 20140128630 A | 11/2014 |
| KR | 20150017693 A | 2/2015 |
| KR | 20160093990 A | 8/2016 |
| KR | 20170038837 A | 4/2017 |
| KR | 101988167 B1 | 6/2019 |
| KR | 20200025290 A | 3/2020 |
| KR | 20200029180 A | 3/2020 |
| KR | 102116664 B1 | 5/2020 |
| KR | 102116968 B1 | 5/2020 |
| KR | 20200056233 A | 5/2020 |
| KR | 102120828 B1 | 6/2020 |
| KR | 102142713 B1 | 8/2020 |
| KR | 102162522 B1 | 10/2020 |
| KR | 102173553 B1 | 11/2020 |
| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 20210052028 A | 5/2021 |
| KR | 102264498 B1 | 6/2021 |
| WO | 0149235 A2 | 7/2001 |
| WO | 0151083 A2 | 7/2001 |
| WO | 2001050387 A1 | 7/2001 |
| WO | 02062211 A2 | 8/2002 |
| WO | 2003043494 | 5/2003 |
| WO | 2006004430 A2 | 1/2006 |
| WO | 2008114291 A1 | 9/2008 |
| WO | 2009008968 A1 | 1/2009 |
| WO | 2014163976 A1 | 10/2014 |
| WO | 2016154318 A1 | 9/2016 |
| WO | 2017166074 A1 | 5/2017 |
| WO | 2018171853 A1 | 9/2018 |
| WO | 2019022706 A1 | 1/2019 |
| WO | 2019204876 A1 | 4/2019 |
| WO | 2020185769 A1 | 3/2020 |
| WO | 2020075190 A1 | 4/2020 |
| WO | 2020130979 A1 | 6/2020 |
| WO | 2020149815 A2 | 7/2020 |
| WO | 2020229705 A1 | 11/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021022003 A1 | 2/2021 |
| WO | 2021038980 A1 | 3/2021 |
| WO | 2021055427 A1 | 3/2021 |
| WO | 2021055491 A1 | 3/2021 |
| WO | 2021061061 A1 | 4/2021 |
| WO | 2021081094 A1 | 4/2021 |
| WO | 2021138620 A1 | 7/2021 |
| WO | 2021216881 A1 | 10/2021 |
| WO | 2021236542 A1 | 11/2021 |
| WO | 2021236961 A1 | 11/2021 |
| WO | 2021262809 A1 | 12/2021 |
| WO | 2022216498 A1 | 10/2022 |
| WO | 2022251420 A1 | 12/2022 |

OTHER PUBLICATIONS

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Claris Healthcare Inc.; Claris Reflex Patient Rehabilitation System Brochure, https://clarisreflex.com/, retrieved from internet on Oct. 2, 2019; 5 pages.

International Searching Authority, Search Report and Written Opinion for International Application No. PCT/US2021/032807, dated Sep. 6, 2021, 11 pages.

Barrett et al., "Artificial intelligence supported patient self-care in chronic heart failure: a paradigm shift from reactive to predictive, preventive and personalised care," EPMA Journal (2019), pp. 445-464.

Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 vol. 97:4.

Lima de Melo Ghisi et al., "A systematic review of patient education in cardiac patients: Do they increase knowledge and promote health behavior change?," Patient Education and Counseling, 2014, pp. 1-15.

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

(56) References Cited

OTHER PUBLICATIONS

Beene et al., "AI and Care Delivery: Emerging Opportunities for Artificial Intelligence to Transform How Care Is Delivered," Nov. 2019, American Hospital Association, pp. 1-12.

Davenport et al., "The Potential for Artificial Intelligence in Healthcare", 2019, Future Healthcare Journal 2019, vol. 6, No. 2: Year: 2019, pp. 1-5.

Ahmed et al., "Artificial Intelligence With Multi-Functional Machine Learning Platform Development for Better Healthcare and Precision Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

Website for "ComfySplints Goniometer Knee", pp. 1-5, retrieved on Sep. 9, 2022 from https://www.comfysplints.com/product/knee-splints/.

Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.

Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.

Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.

Ahmed et al., "Artificial intelligence with multi-functional machine learning platform development for better healthcare and precision medicine," Database, 2020, pp. 1-35.

Davenport et al., "The potential for artificial intelligence in healthcare," Digital Technology, Future Healthcare Journal, 2019, pp. 1-5, vol. 6, No. 2.

Website for "OxeFit XS1", pp. 1-3, retrieved on Sep. 9, 2022 from https://www.oxefit.com/xs1.

Website for "Preva Mobile", pp. 1-6, retrieved on Sep. 9, 2022 from https://www.precor.com/en-us/resources/introducing-preva-mobile.

Website for "J-Bike", pp. 1-3, retrieved on Sep. 9, 2022 from https://www.magneticdays.com/en/cycling-for-physical-rehabilitation.

Website for "Excy", pp. 1-12, retrieved on Sep. 9, 2022 from https://excy.com/portable-exercise-rehabilitation-excy-xcs-pro/.

Website for "OxeFit XP1", p. 1, retrieved on Sep. 9, 2022 from https://www.oxefit.com/xp1.

Jeong et al., "Computer-assisted upper extremity training using interactive biking exercise (iBikE) platform," Sep. 2012, pp. 1-5, 34th Annual International Conference of the IEEE EMBS.

* cited by examiner 20, 120 →

| NAME | PROCEDURE | POST-OP DAY | PAIN | ROM | ALERTS |
|---|---|---|---|---|---|
| Presley, Elvis | Knee | 1 | 6 ☺ | 0.0°/179.0° | ◇ |
| Dalton, Deb | Knee | 8 | | | |
| Upton, Brisa | Knee Surgery | 16 | | | |
| Marvin, Brayan | Knee Replacement | 16 | | | |
| Cole, Jane | Knee Surgery | 19 | | | |
| Smith, Susan | | 22 | | | |
| Mueller, Micheal | Knee Surgery | 23 | | | |
| Tuffree, Nikki | Knee Surgery | 24 | | | |

Patients

🔍 Patient Name  | + Add Patient |  ˅ Rossie Berge

1

Previous    Next

Before We Begin

Please Indicate Your Current Level of Pain Below:

322

0 1 2 3 4 5 6 7 8 9 10

BACK   NEXT

FIG. 10

Before We Begin

Have you noticed any of the following in the last 24 hours?

New trouble or decreased ability to walk?  ◯ Yes  ◯ No

Fever and/or chills?  ◯ Yes  ◯ No

Drainage from surgical site?  ◯ Yes  ◯ No

New redness, swelling, and/or heat?  ◯ Yes  ◯ No

Nausea?  ◯ Yes  ◯ No

< BACK          NEXT >

FIG. 11

Before We Begin

Have you noticed any of the following in the last 24 hours?

Increased pain? ◯ Yes ◯ No

Pain in back of calf? ◯ Yes ◯ No

Reduced range of motion? ◯ Yes ◯ No

Wound/incision splitting apart or opening? ◯ Yes ◯ No

Shortness of breath? ◯ Yes ◯ No

< BACK    NEXT >

You Indicated you are Experiencing:

Wound/Incision Splitting Apart or Opening?

Is this Correct?

YES     NO

FIG. 13

Before We Begin

Please Indicated the Last Time you Took Your Pain Medication.

○ 0 to 2 Hours Ago
○ 2 to 4 Hours Ago
○ 4 to 8 Hours Ago
◉ 8 to 12 Hours Ago
○ 12 to 24 Hours Ago
○ No Pain Medication in the Last 24 Hours

< BACK   NEXT >

Having trouble with pedals?

562 — PLEASE CALL PATIENT SUPPORT RIGHT NOW.
1.888.123.4567

564
CAN'T RESOLVE,
EXIT SESSION

566
GOT IT FIXED,
CONTINUE SESSION

COMPUTER-IMPLEMENTED QUESTIONNAIRE FOR ORTHOPEDIC TREATMENT

CROSS-REFERENCES TO RELATED APPLICATIONS

This application claims priority to and the benefit of U.S. Provisional Application Patent Ser. No. 62/911,638 filed Oct. 7, 2019, titled "Computer-Implemented Questionnaire for Orthopedic Treatment," the entire disclosure of which is hereby incorporated by reference for all purposes.

BACKGROUND

A computer-implemented questionnaire may provide a system with information necessary to safely and effectively perform various aspects of a rehabilitation regimen for a body part. The patient may use a patient user interface for presenting the questionnaire to input responses to questions.

SUMMARY

A computer-implemented system for physical rehabilitation is provided. The computer-implemented system comprises a clinician interface including a patient profile display configured to present data regarding performance, by a patient, of a regimen for a body part, the body part comprising at least one of a joint, a bone, or a muscle group. The computer-implemented system also comprises a patient interface including an output device and an input device for communicating to and from the patient, information regarding the performance of the regimen. The patient interface presents instructions and status information to the patient regarding the performance of the regimen. The patient interface presents a questionnaire soliciting the patient to answer a plurality of questions. One of the plurality of questions pertains to a current physical condition of the patient or a past physical condition of the patient.

A system for remote treatment is also provided. The system for remote treatment includes: a clinician interface comprising a patient profile display configured to present status information regarding a patient; a patient interface including an output device and an input device for communicating information, respectively, to and from a patient; and a treatment apparatus configured to be manipulated by the patient for performing a regimen for a body part, the body part comprising at least one of a joint, a bone, or a muscle group. The patient interface and the treatment apparatus are each configured to enable operation from a patient location geographically separate from a location of the clinician interface. The patient interface presents a questionnaire soliciting a response to a question pertaining to one of a current physical condition of the patient or a past physical condition of the patient.

A patient user interface generated by a computer is also provided. The patient user interface comprises a session period action screen presenting real-time status of measurements regarding a patient's use of a treatment apparatus for performing a regimen for a body part, the body part comprising at least one of a joint, a bone, or a muscle group. The patient user interface also comprises a questionnaire soliciting the patient to answer a plurality of questions pertaining to physical conditions of the patient.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 5 shows an example embodiment of an overview display of a clinician interface;

FIG. 6 shows an example embodiment of a patient profile display of a clinician interface;

FIG. 10 shows an example embodiment of a pain level input screen of a patient interface;

FIG. 11 shows an example embodiment of a first pretreatment questionnaire screen of a patient interface;

FIG. 12 shows an example embodiment of a second pretreatment questionnaire screen of a patient interface;

FIG. 13 shows an example embodiment of a question confirmation screen of a patient interface;

FIG. 14 shows an example embodiment of a third pretreatment questionnaire screen of a patient interface;

FIG. 16 shows an example embodiment of a positioning help screen of a patient interface;

NOTATION AND NOMENCLATURE

Figure 1:
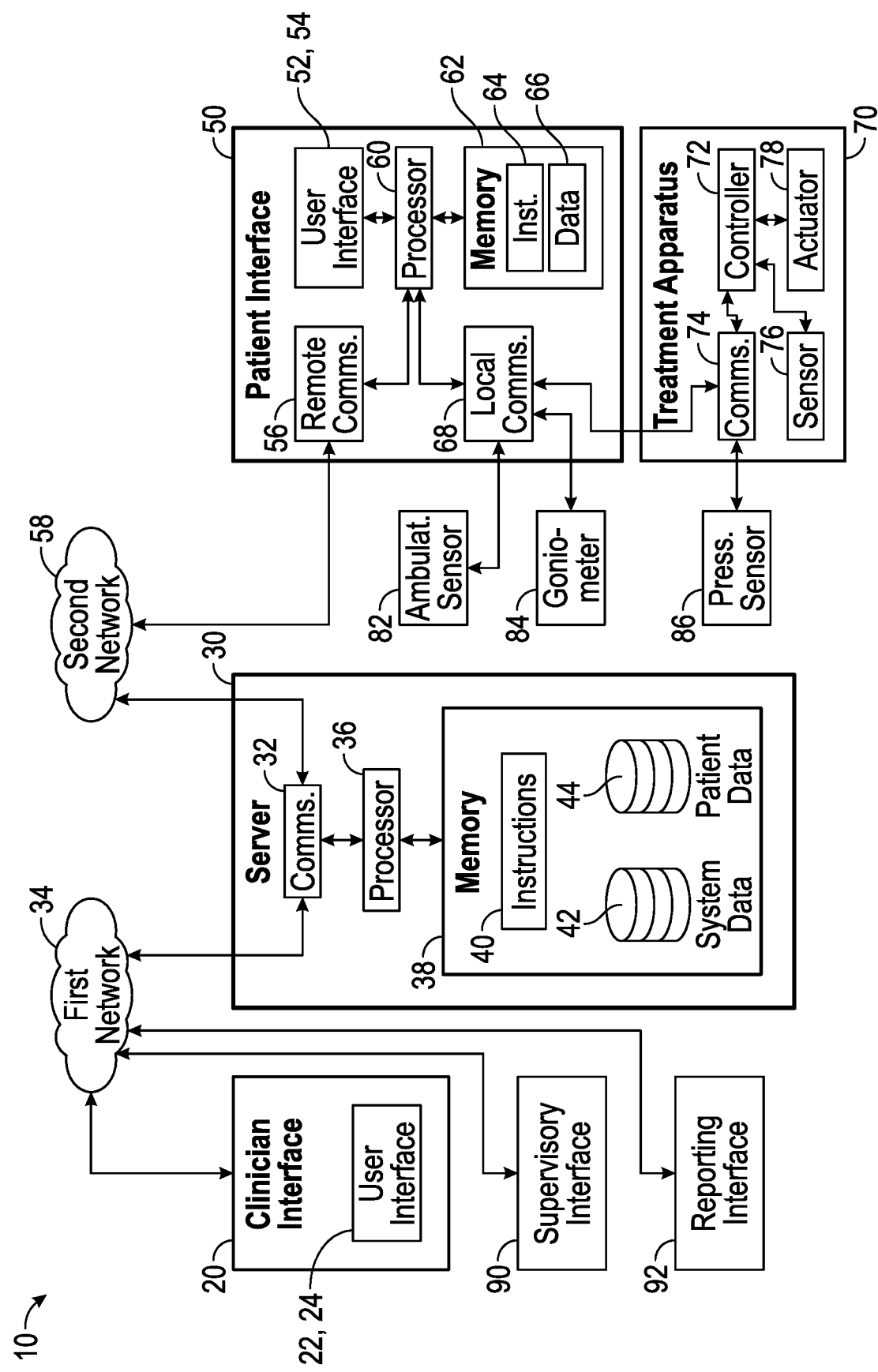
FIG. 1 shows a block diagram of an embodiment of a computer-implemented system for managing a treatment plan.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

Moreover, various functions described below can be implemented or supported by one or more computer programs, each of which is formed from computer readable program code and embodied in a computer readable storage medium. The terms "application" and "program" refer to one or more computer programs, software components, sets of instructions, procedures, functions, methods, objects, classes, instances, related data, or a portion thereof adapted for implementation in a suitable computer readable program code. The phrase "computer readable program code" includes any type of computer code, including source code, object code, and executable code. The phrase "computer readable storage medium" includes any type of medium capable of being accessed by a computer, such as read only memory (ROM), random access memory (RAM), a hard disk drive, a flash drive, a compact disc (CD), a digital video disc (DVD), solid state drive (SSD), or any other type of memory. A "non-transitory" computer readable storage medium excludes wired, wireless, optical, or other communication links that transport transitory electrical or other signals. A non-transitory computer-readable storage medium includes media where data can be permanently stored and media where data can be stored and later overwritten, such as a rewritable optical disc or an erasable memory device.

The terms "transmit," "receive," and "communicate," as well as derivatives thereof, encompass both direct and indirect communication. The terms "transmit," "receive," and "communicate," as well as derivatives thereof, encompass both communication with remote systems and communication within a system, including reading and writing to different portions of a memory device. The term "controller" means any device, system or part thereof that controls at least one operation. Such a controller may be implemented in hardware or a combination of hardware and software and/or firmware. The functionality associated with any particular controller may be centralized or distributed, whether locally or remotely.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment device, a diet regimen for the patient, a medication regimen for the patient, a sleep regimen for the patient, additional regimens, or some combination thereof.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

FIG. 1 shows a block diagram of a computer-implemented system 10, hereinafter called "the system", for physical rehabilitation of a body part of a patient. In some embodiments, the system 10 includes functionality for managing a treatment plan. The treatment plan includes one or more treatment protocols, and each treatment protocol includes one or more sessions. Each session comprises several session periods, with each session period including a particular activity for treating the patient's body part. For example, a treatment plan for post-operative rehabilitation after a knee surgery may include an initial treatment protocol with twice daily stretching sessions for the first 3 days after surgery and a more intensive treatment protocol with active exercise sessions performed four times per day starting four days after surgery.

The system 10 includes a clinician interface 20 for a clinician, such as a doctor, a nurse, a physical therapist, or a technician, to use to review and to configure various aspects of a treatment plan for use in treating a patient. The clinician interface 20 includes a clinician input device 22 and a clinician display 24, which may be collectively called a clinician user interface 22, 24. The clinician input device 22 may include one or more of a keyboard, a mouse, a trackpad, or a touch screen, for example. Alternatively or additionally, the clinician input device 22 may include one or more microphones and voice-based functionalities, with hardware and/or software configured to interpret spoken instructions by the clinician by using the one or more microphones. The clinician input device 22 may include functionality provided by or similar to existing voice-based assistants such as Siri by Apple, Alexa by Amazon, Google Assistant, or Bixby by Samsung. The clinician input device 22 may include other hardware and/or software components. The clinician input device 22 may include one or more general purpose devices and/or special-purpose devices.

The clinician display 24 may take one or more different forms including, for example, a computer monitor or display screen on a tablet, smartphone, or a smart watch. The clinician display 24 may include other hardware and/or software components such as a projector, virtual reality capability, or augmented reality capability etc. The clinician display 24 may incorporate various different visual, audio, or other presentation technologies. For example, the clinician display 24 may include a non-visual display, such as an audio signal, which may include spoken language and/or other sounds such as tones, chimes, and/or melodies which may signal different conditions and/or directions. The clinician display 24 may comprise one or more different display screens presenting various data and/or interfaces or controls for use by the clinician. The clinician display 24 may include graphics, which may be presented by a web-based interface and/or by a computer program or application (App.).

The system 10 also includes a server 30 configured to store and to provide data related to managing the treatment plan. The server 30 may include one or more computers and may take the form of a distributed and/or virtualized computer or computers. In some embodiments, the server 30 may generate aspects of the clinician display 24 for presentation by the clinician interface 20. For example, the server 30 may include a web server configured to generate the display screens for presentation upon the clinician display 24. In some embodiments, the clinician display 24 may be configured to present a virtualized desktop that is hosted by the server 30. The server 30 also includes a first communication interface 32 configured to communicate with the clinician interface 20 via a first network 34. In some embodiments, the first network 34 may include a local area network (LAN), such as an Ethernet network. In some embodiments, the first network 34 may include the Internet, and communications between the server 30 and the clinician interface 20 may be secured via encryption, such as, for example, by using a virtual private network (VPN). In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36. The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan. The patient data stored by the server 30 may also include responses provided by the patient to one or more questions, such as questions answered by the patient at various times before, during, and/or after the treatment plan.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a regimen, such as a physical rehabilitation regimen for improving strength or range of motion of a body part. More specifically, the regimen may be an orthopedic rehabilitation regimen, and the treatment may include rehabilitation of the body part of the patient, such as a joint, a bone, or a muscle group. The body part may include, for example, a spine, a hand, a foot, a knee, or a shoulder. The body part may include a part of a joint, a bone, or a muscle group, such as one or more vertebrae or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force a position, a speed, and /or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

In some embodiments, the patient interface 50 and the treatment apparatus 70 are each configured to operate from a patient location geographically separate from a location of the clinician interface 20. For example, the patient interface 50 and the treatment apparatus 70 may be used as part of an in-home rehabilitation system, which may be monitored remotely by using the clinician interface 20 at a centralized location, such as a clinic or hospital. In some embodiments, either or both of the patient interface 50 and/or the treatment apparatus 70 are configured to communicate with a remote computer, such as the server 30, to receive the treatment plan and to report back to the remote computer with data regarding performance by the patient in following the treatment plan.

Figure 2:
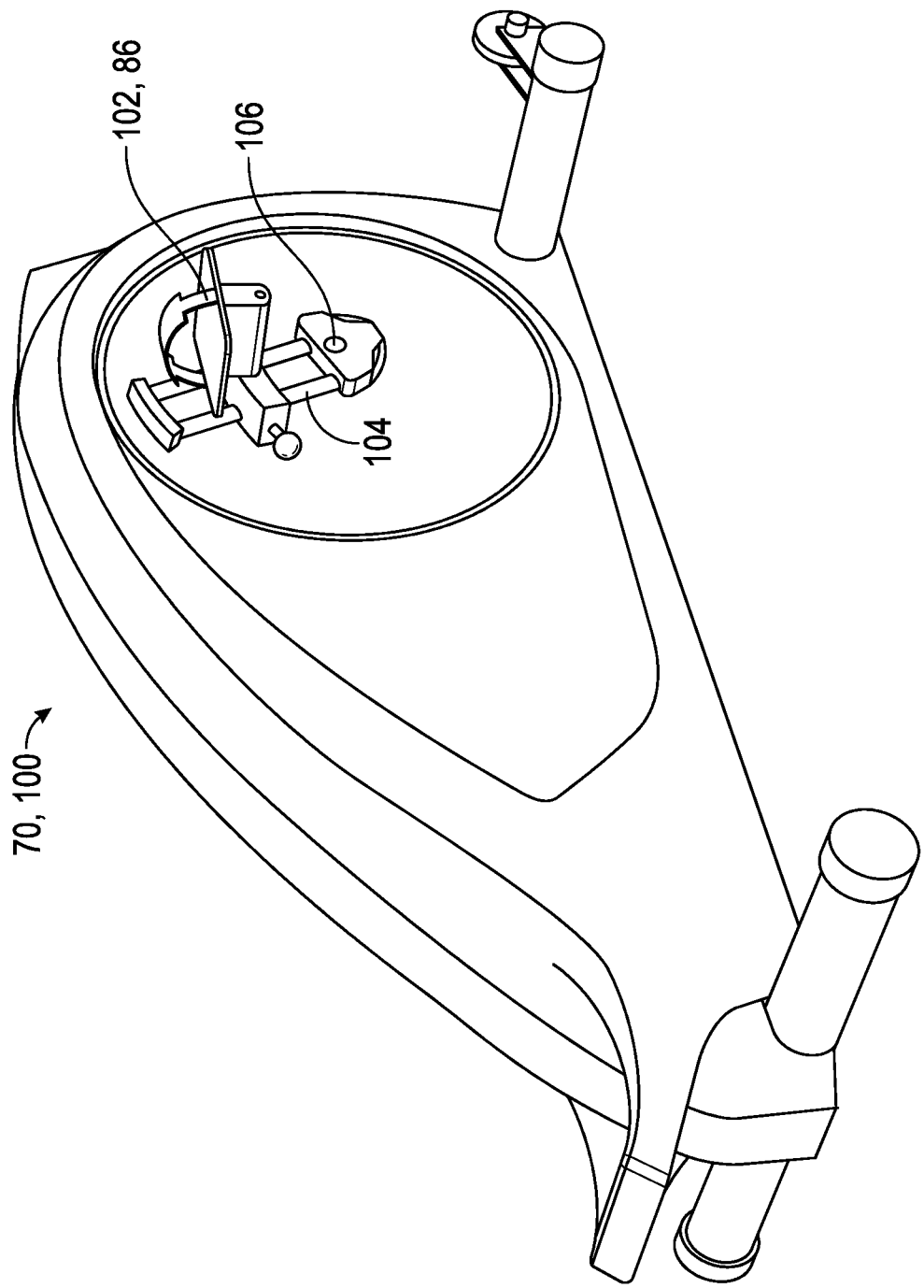
FIG. 2 shows a perspective view of an embodiment of a treatment apparatus.
Figure 3:
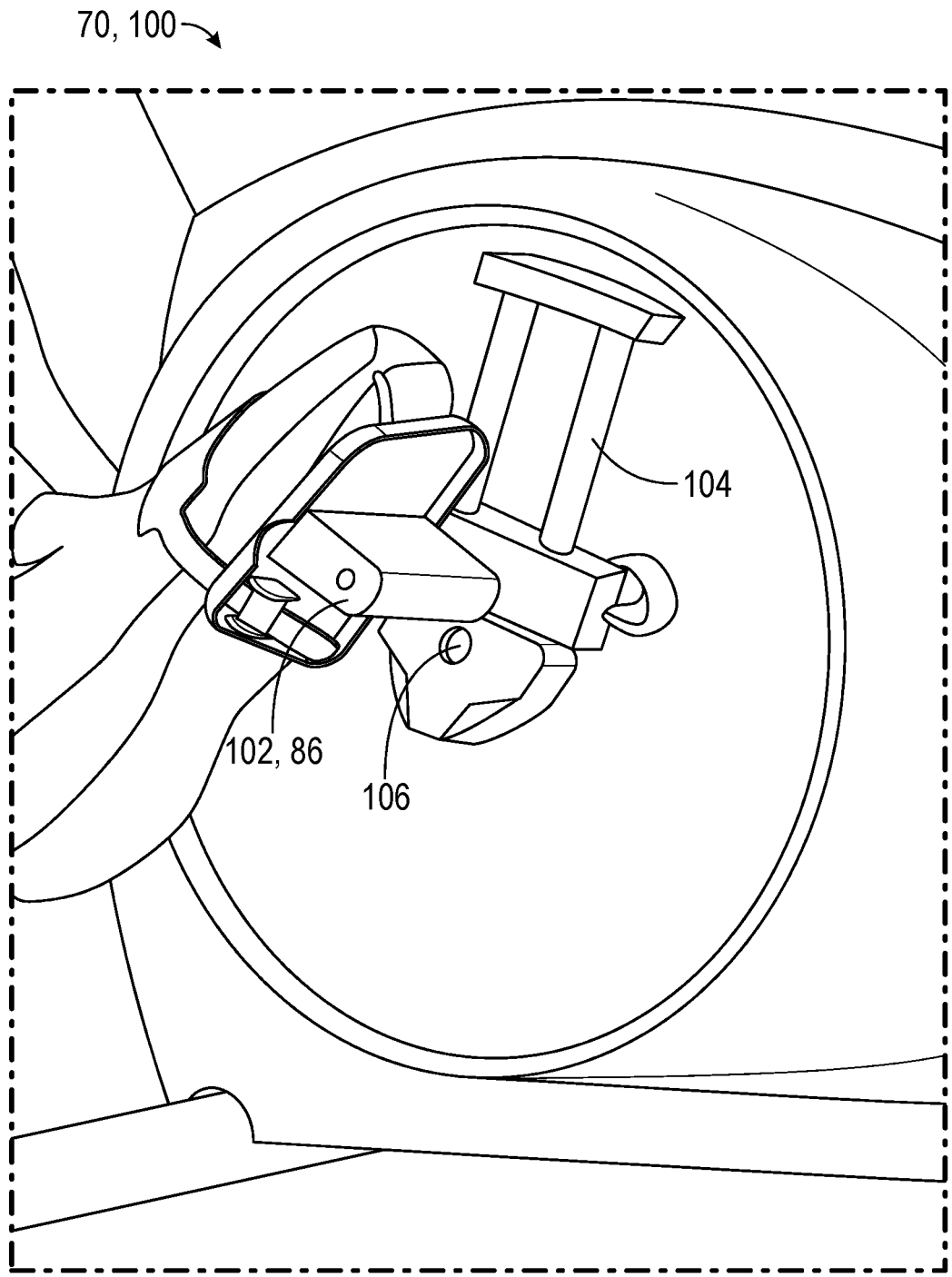
FIG. 3 shows a perspective view of a pedal of the treatment apparatus of FIG. 2.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment apparatus 70 and/or to the patient interface 50.

Figure 4:
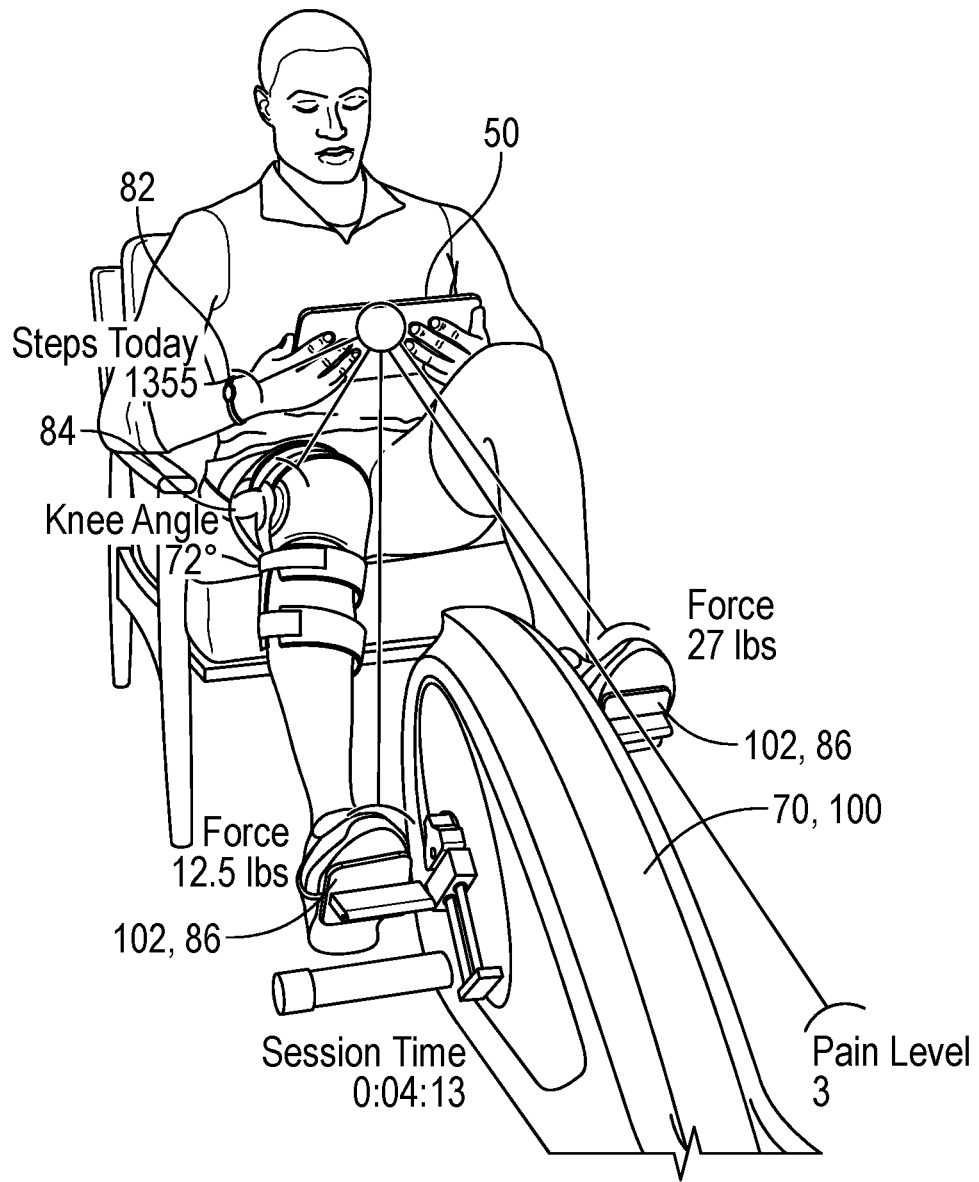
FIG. 4 shows a perspective view of a person using the treatment apparatus of FIG. 2.

FIG. 4 shows a person (a patient) using the treatment apparatus of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 102 with a pressure sensor 86 showing "FORCE 12.5 lbs.," indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation, such as a question, presented upon the patient interface 50.

FIG. 5 is an example embodiment of an overview display 120 of the clinician interface 20. Specifically, the overview display 120 presents summary information regarding each of a plurality of different patients. In some embodiments, and as shown on FIG. 5, the summary information includes an indicator showing a procedure performed upon each of the patients, temporal progress of the patient within the treatment plan (post-op day), an indicator of a last-reported pain level, range-of-motion (ROM) numbers, and an indicator showing if there are any alerts requiring special attention.

Figure 6:
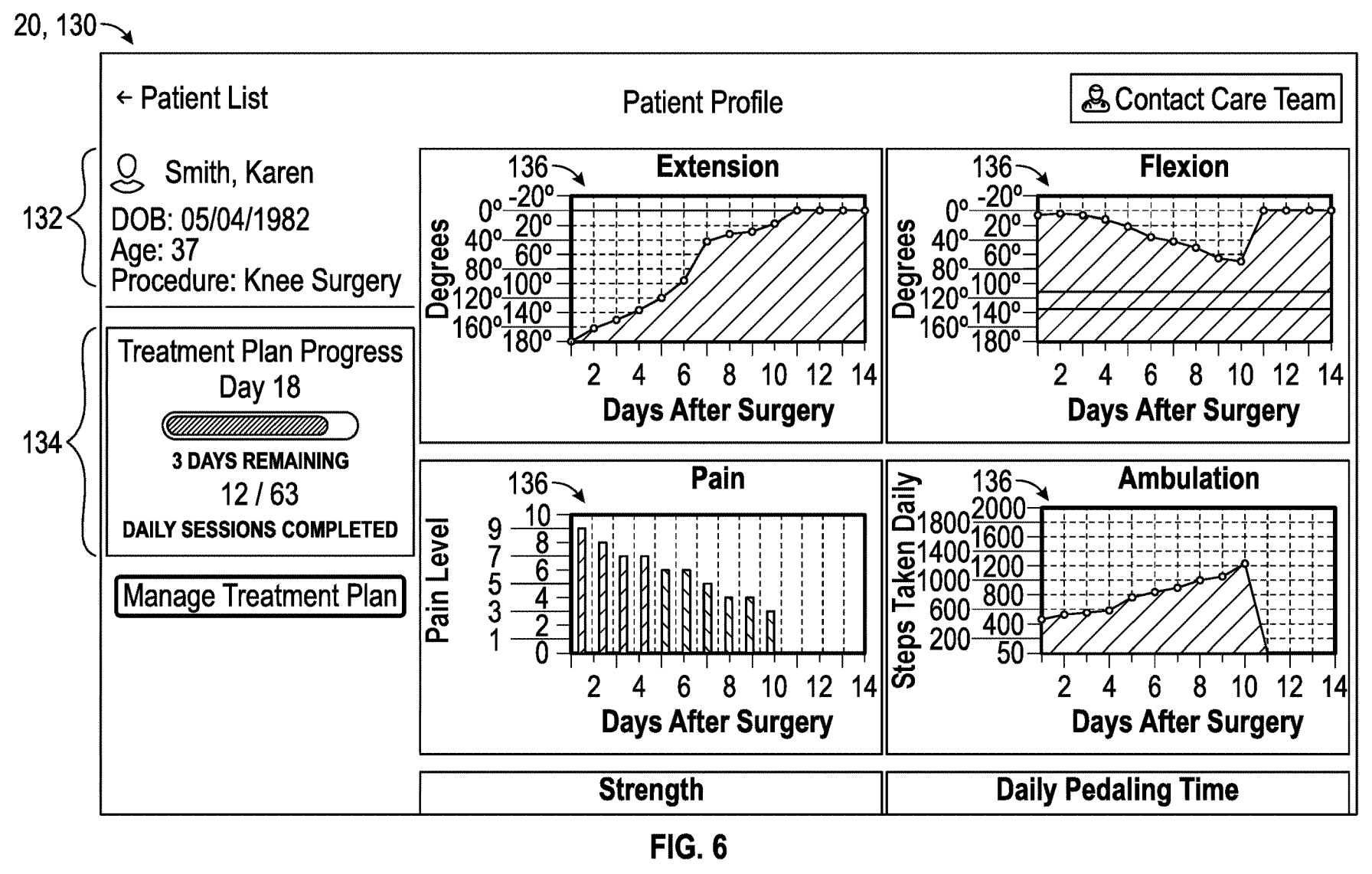
Figure 7:
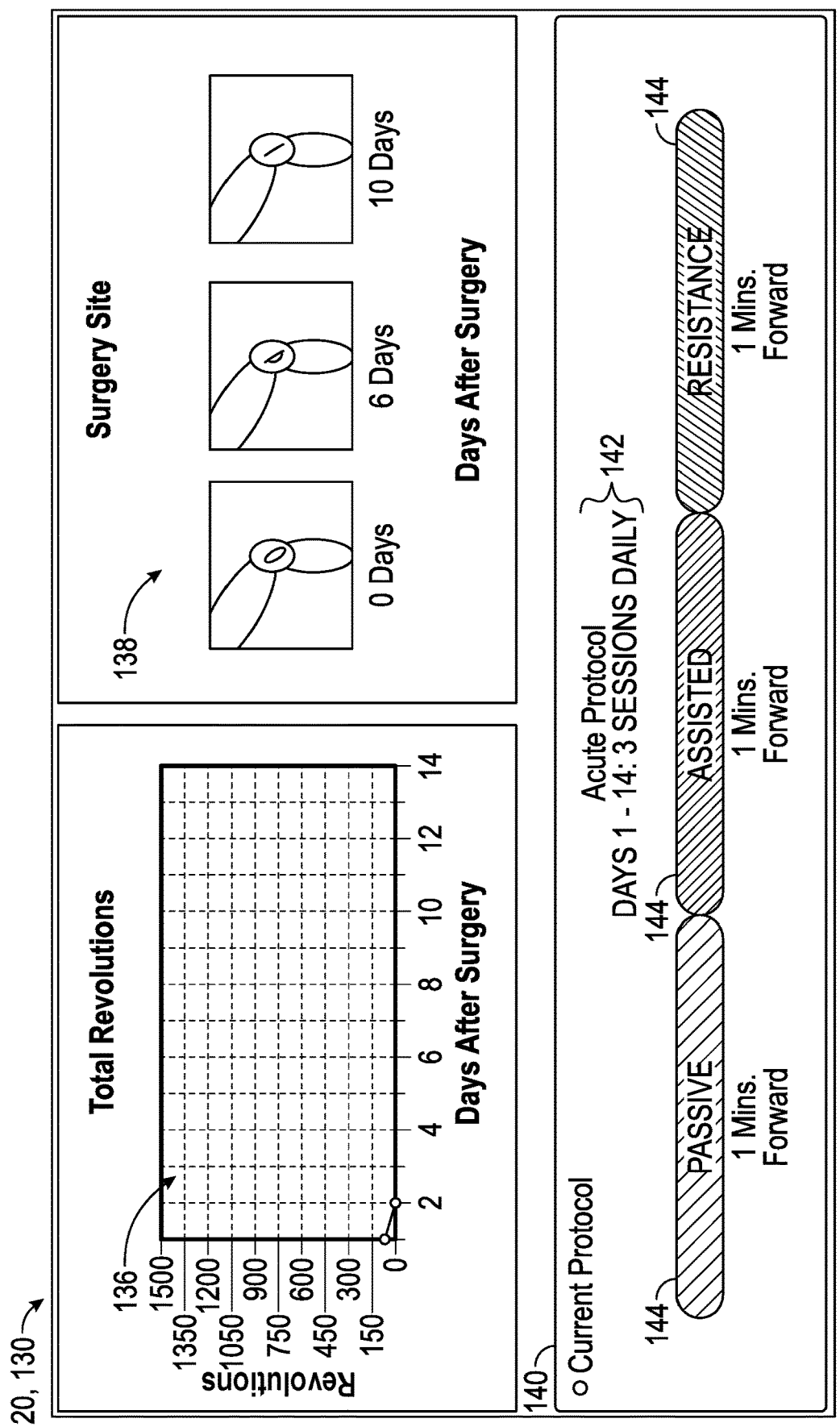
FIG. 7 shows another view of the example patient profile display of FIG. 6.

FIGS. 6-7 show an example embodiment of a patient profile display 130 of the clinician interface 20. The example patient profile display 130 includes a patient summary 132 with the patient's name, date of birth (DOB), age, a description of a procedure performed or to be performed on the patient, e.g., "Knee surgery", and a picture of the patient, if available. The example patient profile display 130 also includes a treatment progress summary 134, showing one or more indicators of progress within a treatment regimen or plan. The example treatment progress summary 134 shown on FIG. 6 includes textual progress summaries, "DAY 18", "3 days remaining", "12/63 DAILY SESSIONS COMPLETED", as well as graphical progress summaries in the form of horizontal bar graphs, which may also be called progress bars.

The example patient profile display 130 presents information regarding a treatment history of the patient. For example, the example patient profile display 130 includes a plurality of different treatment graphs 136 showing the effect of various treatment parameters over time. The treatment graphs 136 shown in the example patient profile display 130 of FIGS. 6-7 include extension (angle), flexion (angle), pain (0-10 scale), ambulation (steps/day), and total revolutions (i.e., revolutions performed on the stationary cycling machine 100). The patient profile display 130 shown on FIG. 7 also includes a pictorial history 138, showing one or more images of the surgical site for reference by a clinician or other healthcare professional in reviewing post-operative progress. The images in the pictorial history 138 may be taken by the patient and/or by a clinician or other healthcare professional. For example, the first picture may be taken by a member of the surgical staff, and subsequent pictures may be taken by the patient and/or the rehabilitation clinician. The example patient profile display 130 shown on FIG. 7 also includes a protocol summary display 140 showing a summary overview of a treatment protocol to be performed by the patient. The example protocol summary display 140 includes a protocol heading 142 with a protocol name, e.g. "Acute Protocol." The protocol heading 142 also includes overview information regarding how and when the protocol is to be performed, e.g. "Days 1-14, 3 sessions daily." The protocol summary display 140 also includes several protocol session icons 144, each indicating details of an activity to be performed within a protocol session, e.g., "Passive", "Active", or "Resistance", together with other information regarding the protocol session, such as a direction (forward/reverse), and an amount of time that each protocol session is prescribed to be performed.

Figure 8:
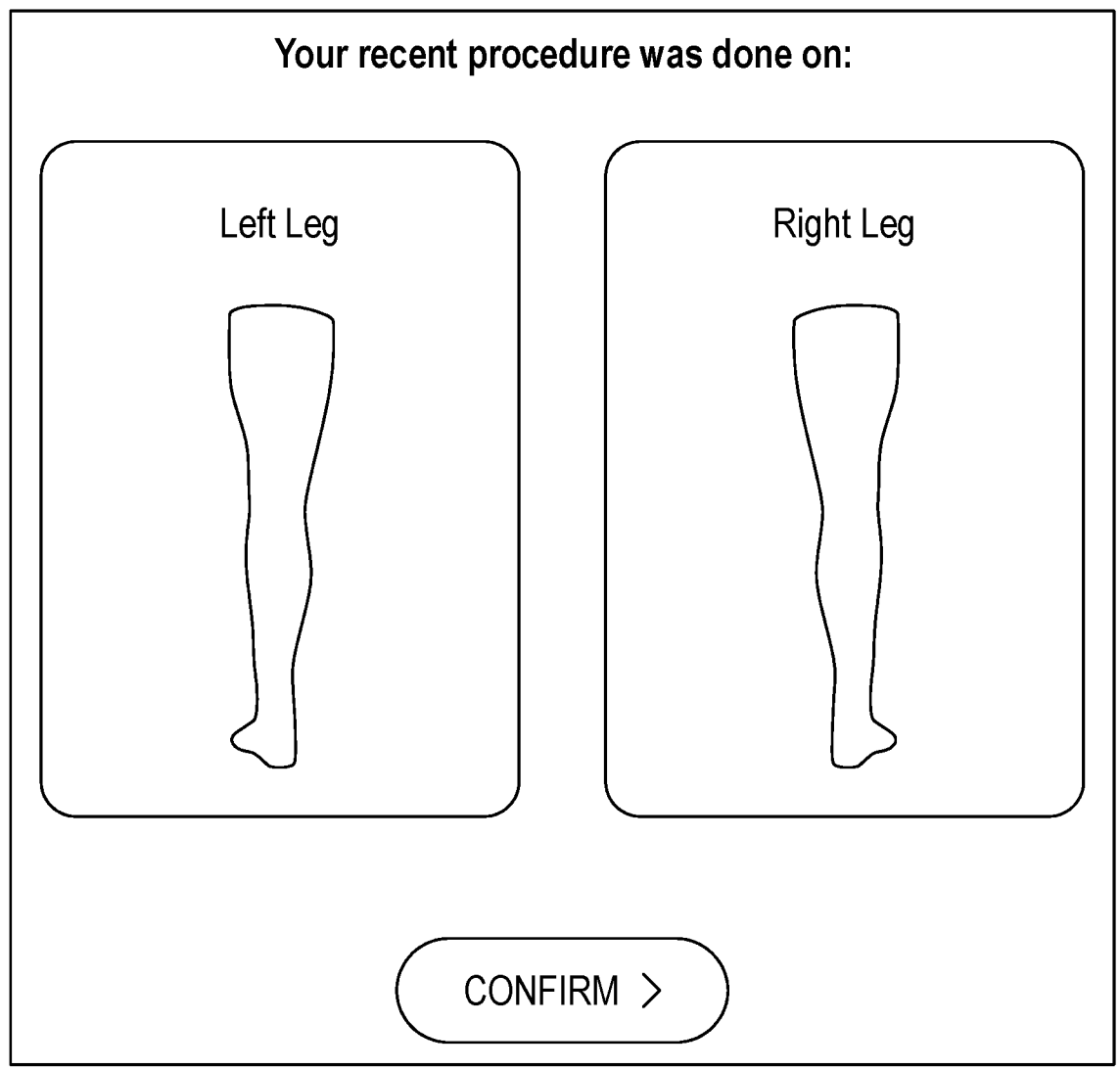
FIG. 8 shows an example embodiment of a body part confirmation screen of a patient interface.

FIG. 8 shows an example of a body part confirmation screen 240 of the patient interface 50. The patient may be asked to confirm the particular body part to be treated in order to ensure that the treatment plan is correct for that particular patient. The body part confirmation screen 240 is also used to ensure that the patient is aware of the body part to be treated (i.e., to set the patient's expectations) to minimize risk of an unexpected event that could result in an adverse outcome. If the patient selects a body part that does not comport with the treatment plan, the treatment session may be cancelled, and a notice to the clinician may be generated. The patient may be asked to confirm their selection and, then, given the opportunity to change their selection to ensure that treatment is not cancelled and/or that the clinician is not notified in case of a mis-selection.

Figure 9:
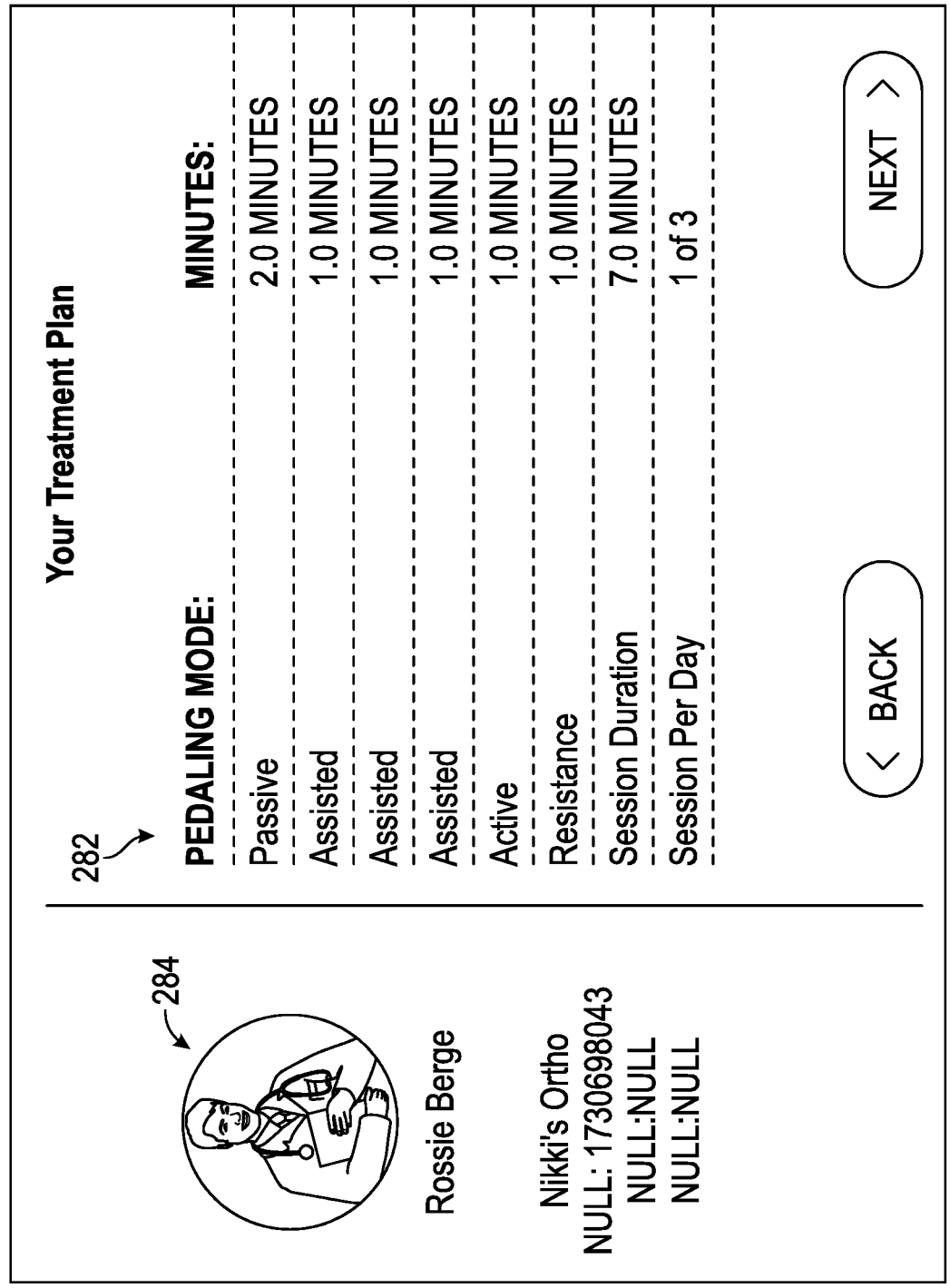
FIG. 9 shows an example embodiment of a treatment plan overview screen of a patient interface.

FIG. 9 shows an example of a treatment plan overview screen 280 of the patient interface 50. Specifically, the treatment plan overview screen 280 includes a session summary 282 with a listing of the session periods and their respective durations (in minutes), with the total session duration, and with a display of the sessions per day. The treatment plan overview screen 280 includes a practitioner contact data 284 with a picture and phone numbers for a practitioner that the patient may contact for help. The practitioner may be, for example, an orthopedic surgeon and/or a physical therapist.

The patient interface 50 presents a questionnaire 320, 360, 400, 480, 720 soliciting the patient to answer a plurality of questions. In some embodiments, the questionnaire 320, 360, 400, 480, 720, or a portion thereof, is presented to the patient before the treatment session. Alternatively or additionally, the questionnaire 320, 360, 400, 480, 720, or a portion thereof, may be presented to the patient after or during the treatment session. For example, one or more questions may be presented for the patient to answer using the patient interface 50 while a training session is in progress or during a break between session periods. In some embodiments, one or more of the questions of the questionnaire 320, 360, 400, 480, 720 pertains to a current physical condition of the patient. For example, as shown in FIG. 10, one of the questions may ask the patient to rate their current pain level. In some embodiments, one or more of the questions of the questionnaire 320, 360, 400, 480, 720 pertains to a past physical condition of the patient. For example, as shown in FIGS. 11-12, the questionnaire 320, 360, 400, 480, 720 may ask about various physical conditions that the patient has noticed or experienced in the past twenty-four hours that could affect the patient's ability to perform the rehabilitation regimen.

FIG. 10 shows an example embodiment of a pain level input screen 320 of the patient interface 50. The pain level input screen 320 includes a pain level selector 322 for the patient to indicate his or her pain level. The example pain level selector 322 is a slider that the patient can use to select a pain level of 0 (no pain) to 10 (maximum pain). The pain level input screen 320 may include other inputs, such as a numeric input or check boxes. Graphics, such as happy-to-sad face icons may help to clarify that 10 is the highest level of pain. A similar pain level input screen 320 may be presented before, during, and/or after a treatment session for tracking the effect of the session on the patient's pain level.

FIGS. 11-12 show an example embodiment of a first pretreatment questionnaire screen 360 and a second pretreatment questionnaire screen 400 of the patient interface 50, respectively. The pretreatment questionnaire screens 360, 400 may help to determine if the patient has any conditions that may adversely impact their ability to perform the training session. For example, the pretreatment questionnaire screens 360, 400 may include one or more questions that relate to the patient's ability to use the treatment apparatus 70. Specifically, the example pretreatment questionnaire screens 360, 400 of FIGS. 11-12 ask the patient whether he/she has noticed any of several different conditions in the last 24 hours. FIGS. 11-12 provide Yes/No inputs for the patient to indicate a presence of each of the different conditions. The conditions asked about include: "New trouble or decreased ability to walk," "Fever and/or chills," "Drainage from surgical site," "New redness, swelling, and/or heat," "Nausea," "Increased pain," "Pain in back of calf," "Reduced range of motion," "Wound/incision splitting apart or opening," and "Shortness of breath." These are merely examples of different conditions that may be asked of the patient before beginning the rehabilitation regimen. In some embodiments, before the patient is authorized to use the treatment apparatus 70, predetermined responses must be provided on the pretreatment questionnaire screens 360, 400.

In some embodiments, the system 10 is configured to take an action in response to a selected answer or response to one or more of the questions. The action, taken in response to a selected answer or response may include inhibiting or mitigating operation of the treatment apparatus 70. The action may include transmitting an alert to the clinician, stopping the treatment apparatus 70, and/or locking the treatment apparatus 70 to prevent it from being used until the clinician or another authorized person is able to verify that it is safe for the patient to proceed with the training session. For example, affirmative responses to either of the "[Have you noticed] wound/incision splitting" and/or the "[Have you noticed] shortness of breath" inquiries may prevent the patient from proceeding with the treatment until the clinician first verifies that it is safe for the patient to proceed.

The patient interface 50 may present a confirmation prompt for the patient to confirm the selected response before the action is taken. The confirmation prompt may take the form of a question confirmation screen 440, such as the one shown in FIG. 13. For example, a selected response that indicates a potential serious medical issue, such as "shortness of breath," may require confirmation before the system locks 10 the treatment apparatus 70 and/or generates an alert if the patient selects or otherwise indicates, in error, that particular response. The confirmation prompt may take other forms, such as visual or audible warnings, which may include a description of one or more consequences of the particular response provided. Additionally or alternatively, the patient interface 50 may present additional instructions to the patient in response to particular answers or responses to given ones of the questions. For example, if the patient indicates that they have experienced wound/incision splitting apart or opening, the patient may be prompted to take one or more pictures of the wound for evaluation by a clinician. In some embodiments, the patient interface 50 may provide instructions for using a camera, which may be integral with the patient interface 50, to capture one or more images and/or video of the wound.

Alerts transmitted to the clinician, such as alerts generated and/or transmitted in response to a particular answer or response to one or more of the questions, may include an alert message upon the clinician interface 20. Such an alert message may include a description of the question and/or the response to the question. In some cases, the alert message may also include an identification of the patient. In other cases, the identification of the patient may be omitted, for example, where the patient's identification would violate privacy requirements. Such an alert message may be presented within an overview display 120, as shown, for example, on FIG. 5. Additionally or alternatively, alert messages generated in response to the patient's answer or response to one or more questions may include an instant notification to the clinician on the user interface. Such an instant notification may include a visual notification, such as a popup message or an animation, within a predetermined region of the clinician display 24. Such alert messages may also be accompanied by an audio notification, such as a sound or a voice prompt, played by a speaker of the clinician interface 20.

In some embodiments, the alert generated and/or transmitted in response to a particular answer or response may comprise a real-time communication to the clinician outside of the clinician interface 20. For example, the system 10 may communicate an alert message to the clinician using a communication message, such as a pager message or a text message or an email. The alert message may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject". For example, an alert message may direct the clinician that a particular type of alert exists, such as a patient reporting wound splitting, without identifying which patient made the report. The alert message may direct the clinician to check the clinician interface 20 for more specific details regarding the alert.

FIG. 14 shows an example embodiment of a third pretreatment questionnaire screen 480 of the patient interface 50. Specifically, the third pretreatment questionnaire screen 480 requests the patient to indicate when they last took pain medication. This question may be used to compensate for the effects of pain medication on reported pain level and/or other performance parameters.

Figure 15:
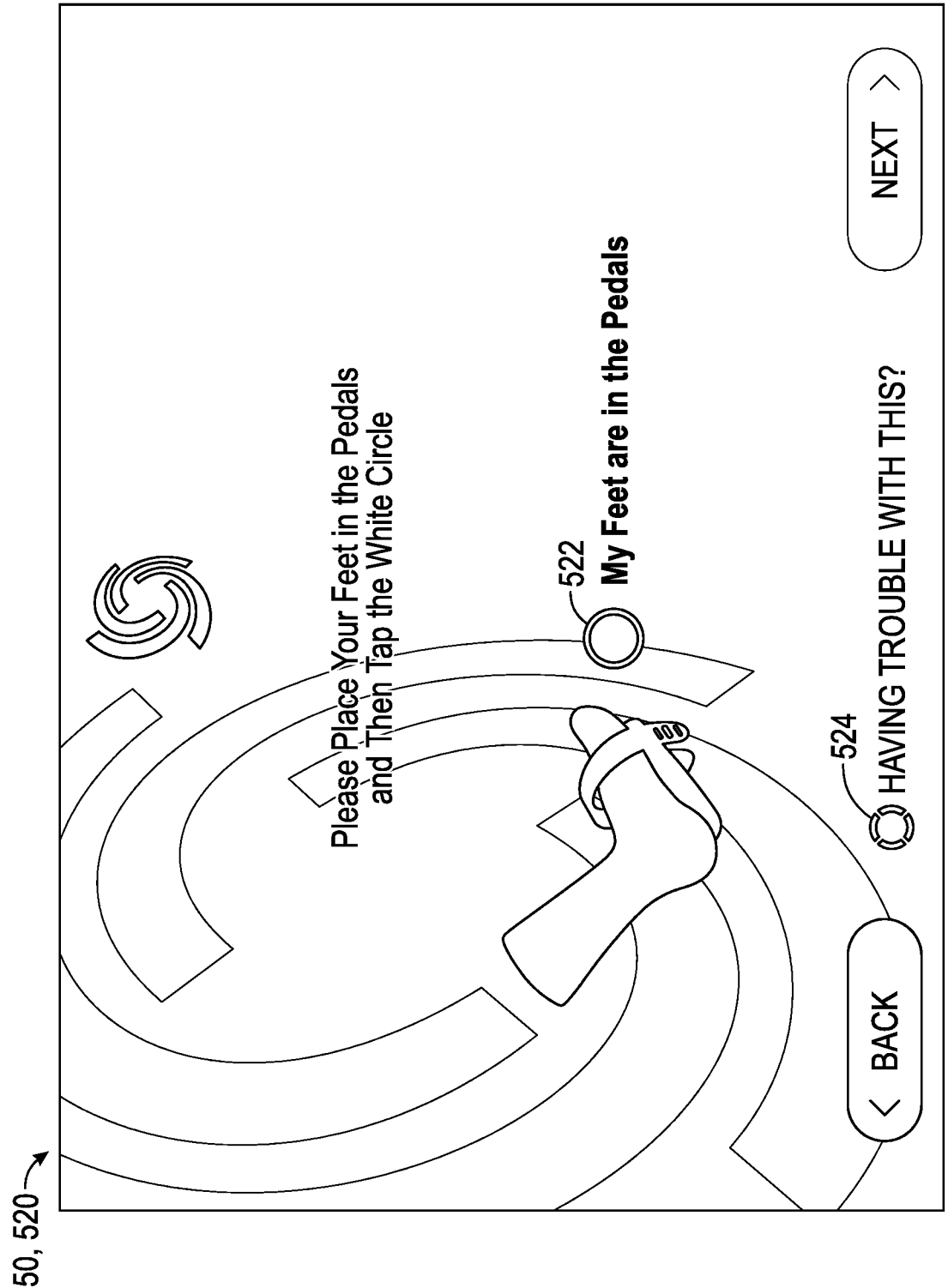
FIG. 15 shows an example embodiment of a positioning confirmation screen of a patient interface.

FIG. 15 shows an example embodiment of positioning confirmation screen 520 of the patient interface 50. This screen 520 is the beginning of a guided walk-through for the patient to use the treatment apparatus 70. Specifically, this screen 520 includes written instructions to guide the patient in placing their feet in the pedals 102 of a stationary cycling machine 100. In some embodiments, this screen 520 may include graphics, such as pictures or animations to help the patient perform particular actions for using the treatment apparatus 70. Screen 520 includes a position confirmation selector 522 for the patient to indicate that they are in position to use the treatment apparatus 70. Screen 520 also includes a trouble button 524 for the patient to indicate that they are having trouble getting in position to use the treatment apparatus 70.

In some embodiments, the patient interface 50 may present a help display 560 in response to occurrence of a triggering event pertaining to the patient's use of the treatment apparatus 70. The help display 560 may include a first control 564, 642, such as a "STOP" button, for the patient to stop using the treatment apparatus 70 and/or to request additional help in using the treatment apparatus 70. The help display 560 may also include a second control 566 for the patient to continue using the treatment apparatus.

FIG. 16 shows an example embodiment of a help screen 560 in the form of a positioning help screen 560. This help screen 560 may be shown in response to the user selecting the trouble button 524 on the positioning confirmation screen 520. The help screen 560 may automatically be displayed if the patient fails to select the position confirmation selector 522 within a predetermined period of time. In some embodiments, an intermediate screen such as a popup asking if the patient needs more time may be displayed before the help screen 560 is shown. The help screen 560 includes assistance instructions 562 for the patient to obtain assistance for using the treatment apparatus 70. In some embodiments, the assistance instructions 562 may include a phone number. The assistance instructions 562 may also include other items, such as a link to a video conference with someone able to help the patient, and/or a link to a video or animated walk-through with detailed instructions for performing a particular action to use the treatment apparatus 70. The particular action may include, for example, placing the feet in the pedals. The help screen 560 may also include a first control 564, which may take the form of an exit button, which the patient can use to stop the treatment session in case they are unable to resolve their issue with using the treatment apparatus 70. Use of the first control 564 may generate an alert to the clinician. The help screen 560 also includes a second control 566, which may take the form of a proceed button, that the patient can use to indicate that they have resolved their issue and are able to proceed with the treatment session.

Figure 17:
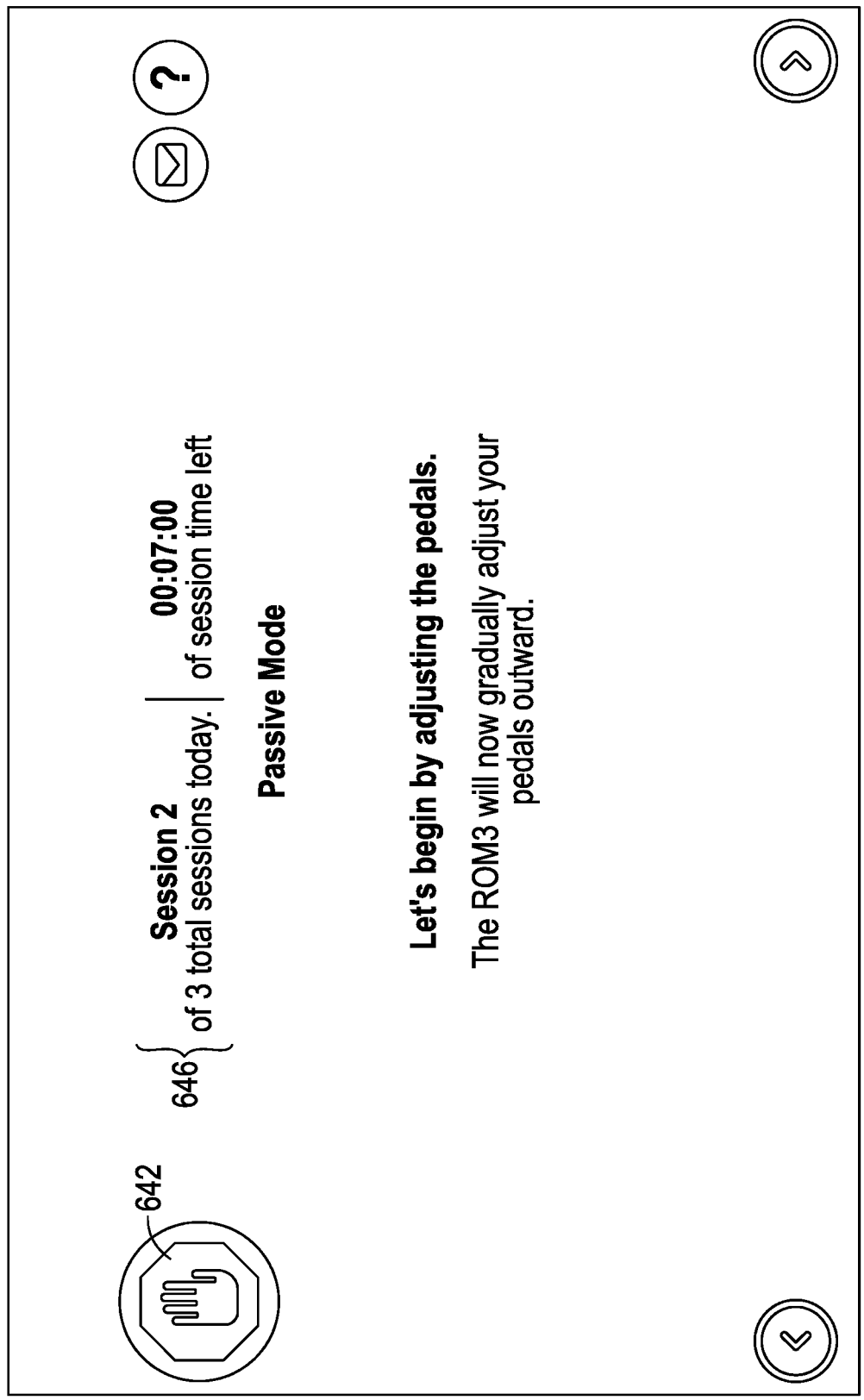
FIG. 17 shows an example embodiment of an adjustment introduction screen of a patient interface.
Figure 18:
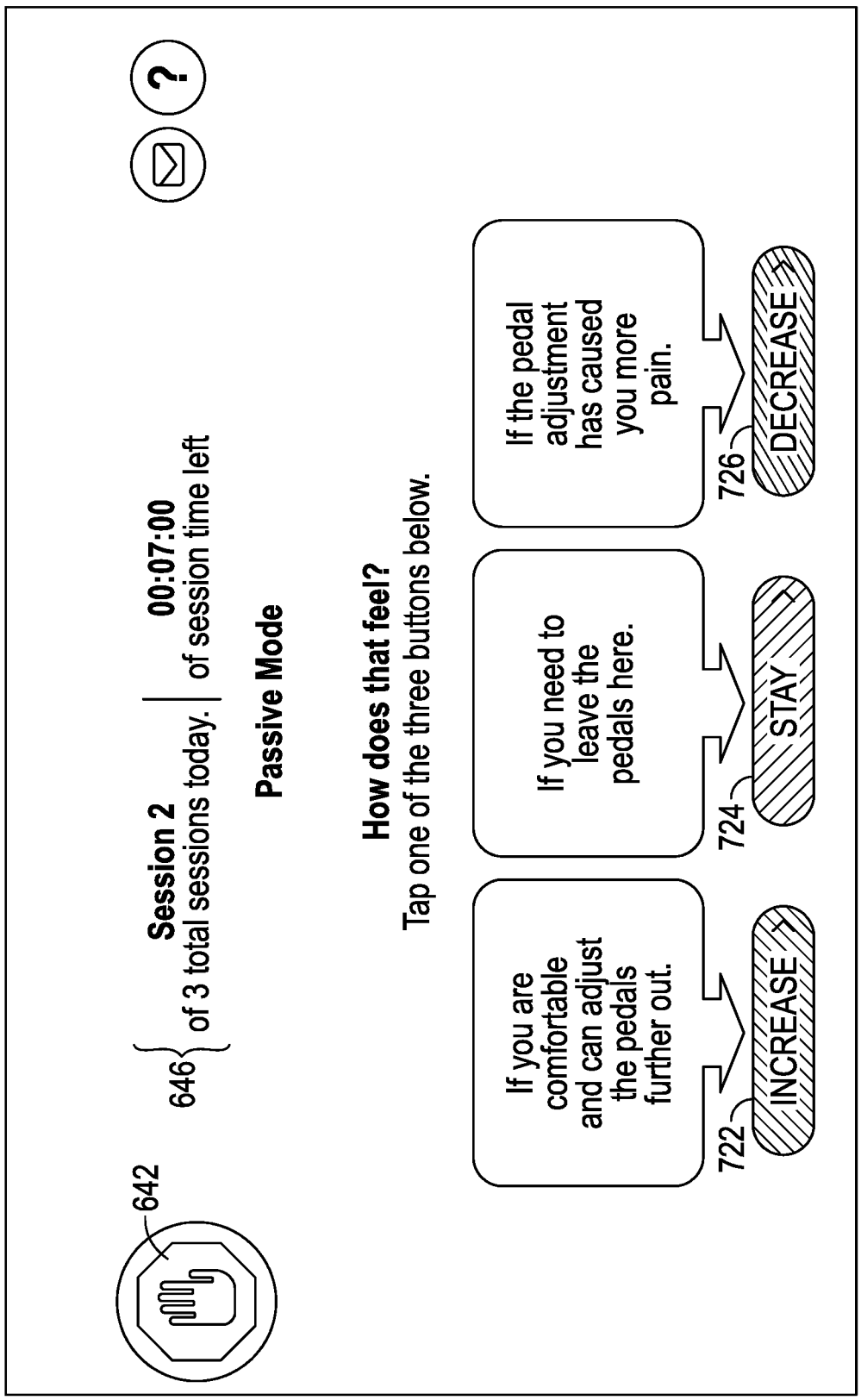
FIG. 18 shows an example embodiment of an adjustment confirmation screen of a patient interface.

FIG. 17 shows an example embodiment of an adjustment introduction screen 680 of the patient interface 50. The adjustment introduction screen 680 includes text and/or graphics indicating various adjustments to be performed by the treatment apparatus 70. In the example shown, the adjustments include the treatment apparatus 70 that is a stationary cycling machine 100 that automatically moves the pedals 102 outwardly to a predetermined position for the session period. FIG. 18 shows an example embodiment of an adjustment confirmation screen 720 of the patient interface 50. The adjustment confirmation screen 720 includes text and/or graphics requesting the patient to confirm their satisfaction with the position of the treatment apparatus 70 during and/or after the automatic adjustments are made. The adjustment confirmation screen 720 includes an increase button 722 that the patient may select to indicate a desire to change the position of the treatment apparatus 70 such as, for example, to increase the radius of the pedal 102 on the pedal arm 104. The adjustment confirmation screen 720 also includes a stay button 724 that the patient may select to indicate acceptance of the position of the treatment apparatus 70. The adjustment confirmation screen 720 also includes a decrease button 726 that the patient may select to indicate a desire to change the position of the treatment apparatus 70. For example, if the patient experiences pain or discomfort with the initial position, he or she may change the position using the decrease button 726 until the pain or discomfort is alleviated.

Figure 19:
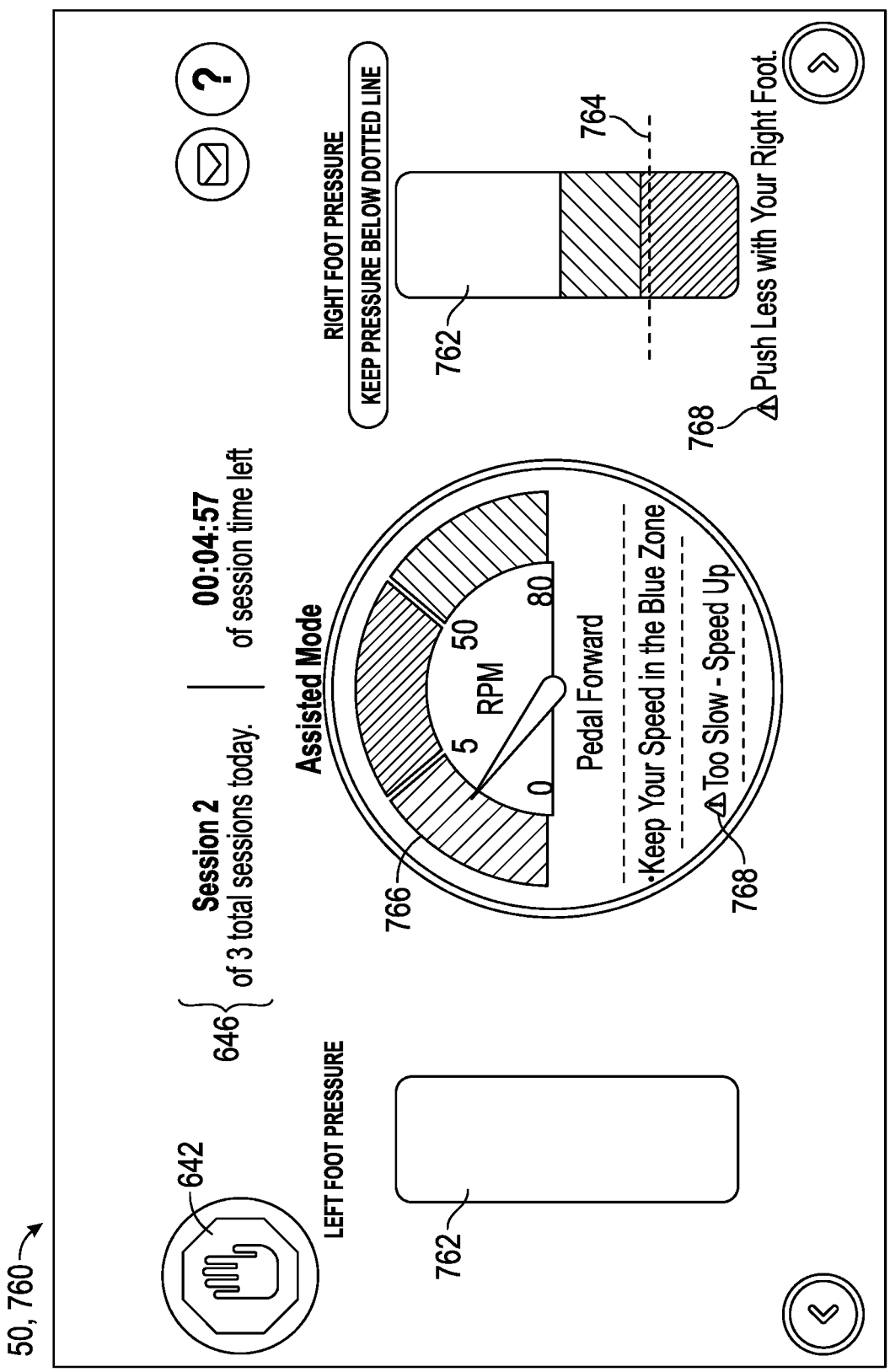
FIG. 19 shows an example embodiment of a session period action screen of a patient interface.

FIG. 19 shows an example embodiment of a session period action screen 760 of the patient interface 50. This screen 760 is displayed while a given session period is in progress. It includes pressure indicators 762 showing an amount of pressure or force applied by each foot. The pressure indicators 762 show the pressures of the patient's feet upon the pedals 102 as measured by the pressure sensors 86. The pressure indicators 762 are shown as bar graphs, but other types of displays may be used, such as rotary gauges and/or numeric indicators. The pressure indicators 762 may also include a target pressure indicator 764 representing a target pressure value which may be determined by the clinician using an associated session parameter control 178 on the clinician interface 20.

The session period action screen 760 also includes a speed indicator 766 showing a speed that the pedals 102 are turning, as measured by an internal sensor 76 of the stationary cycling machine 100. The speed indicator 766 is shown as a rotary gauge, but other types of displays may be used, such as a bar graph and/or a numeric indicator. The speed indicator 766 includes an optimal or desired speed range, which may be determined by the clinician using an associated session parameter control 178 on the clinician interface 20. The session period action screen 760 may present prompts or messages 768 to enable the user to change the pressure and/or speed if either of those parameters is outside of a predetermined range.

In some embodiments, the patient interface 50 may present a mid-treatment questionnaire during a treatment session, the questionnaire configured to solicit responses to one or more questions. The mid-treatment questionnaire may include one or more questions that relate to the patient's ability to use the treatment apparatus 70. In some embodiments, the mid-treatment questionnaire may be presented in response to occurrence of a triggering event, the triggering event pertaining to the patient's use of the treatment apparatus 70.

In some embodiments, a computer, such as the server 30, is configured to automatically modify the treatment plan 154 in response to satisfaction by the patient of a predetermined condition. For example, the treatment plan 154 may be limited in speed, velocity, or pressure settings or number of sessions per day until a predetermined condition is satisfied. In another example, the treatment plan 154 may include only certain types of session periods, such as passive type exercises, until the predetermined condition is satisfied. The predetermined condition may include, for example, a successful post-operative checkup; or completion of a predetermined number of sessions or satisfying a performance benchmark within the treatment plan. Such a benchmark may include, for example, walking X number of steps in a day, or some given RPM speed or a given number of pounds of force using the treatment apparatus 70. In some embodiments, the computer is configured to increase at least one of a frequency, a duration, or an intensity of an aspect of the treatment plan 154 in response to performance or occurrence of the triggering event. In some embodiments, the computer is configured to decrease at least one of a frequency, a duration, or an intensity of an aspect of the treatment plan 154 in response to a performance or occurrence of the triggering event. The triggering event may include, for example, the patient reporting pain in excess of a given value, or an inability to complete one or more activities within the treatment plan 154, or a sudden decrease in walking performed by the patient.

In some embodiments, the patient interface 50 may provide a prompt to the patient in response to occurrence of the predetermined condition. The prompt may take the form of a help display 560, and/or a questionnaire, such as the mid-treatment questionnaire, soliciting responses to one or more questions. In some embodiments, the help display 560 may be configured to include a questionnaire for soliciting responses to one or more questions. In some embodiments, a timer or counter may generate the triggering event. For example, the prompt may be presented to the patient at periodic time intervals, or after each of a predetermined number of repetitions of a given exercise. The triggering event may include the occurrence or non-occurrence of a measurement by an internal sensor 76 of the treatment apparatus 70. For example, in a session period where the patient is expected to maintain the stationary cycling machine at a speed of between 40 and 50 RPM, the predetermined condition may include the cycling machine operating below 30 RPM for a period of 5 seconds. In that case, the patient interface 50 may provide a prompt, such as a help display 560, asking the patient if they are having trouble or pain in performing the activity. The prompts may narrow down a problem. For example, if the patient is unable to perform a given activity, then a computer, such as the server 30, may automatically modify the treatment plan 154 to include activities that are easier for the patient to complete, such as only passive or only assisted session periods. Alternatively, the treatment plan 154 may be suspended until the clinician or another qualified person, such as an orthopedic surgeon, directs the system 10 to re-enable the treatment plan 154. Additionally or alternatively, the patient's responses to the prompts may generate an alert to the clinician.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Any of the systems and methods described in this disclosure may be used in connection with rehabilitation. Rehabilitation may be directed at cardiac rehabilitation, rehabilitation from stroke, multiple sclerosis, Parkinson's disease, a brain injury, a spinal cord injury, a spinal cord disease, a joint injury, a joint disease, or the like. Rehabilitation can further involve muscular contraction improving blood flow and lymphatic flow, engaging the brain and nervous system to control and affect a traumatized area to increase the speed of healing, reversing or reducing pain, reversing or reducing stiffness, recovering range of motion, cardiovascular engagement to stimulate the release of pain blocking hormones and encourage freshly oxygenated blood flow to aid in an overall feeling of well-being. Rehabilitation may be provided for individuals of average height in reasonably good physical condition having no substantial deformities, as well as individuals more typically in need of rehabilitation, such as those that are elderly, obese, injured and/or have a severely limited range of motion. Unless expressly stated otherwise, is to be understood that rehabilitation includes prehabilitation (also referred to as "pre-habilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. Performance of the one or more sets of exercises may be required in order to qualify for an elective surgery, such as a knee replacement. The patient may prepare an area of his or her body for the surgical procedure by performing the one or more sets of exercises, thereby strengthening muscle groups, improving existing muscle memory, reduce pain, reduce stiffness, establishing new muscle memory, enhancing mobility (i.e., improve range of motion), improving blood flow, and/or the like.

Consistent with the above disclosure, the examples of assemblies enumerated in the following clauses are specifically contemplated and are intended as a non-limiting set of examples.

1. A computer-implemented system for physical rehabilitation, comprising: a clinician interface comprising a patient profile display, the patient profile display configured to present data regarding performance, by a patient, of a regimen for a body part, the body part comprising at least one of a joint, a bone, or a muscle group; a patient interface including an output device and an input device for communicating to and from the patient, information regarding the performance of the regimen; the patient interface presenting instructions and status information to the patient regarding the performance of the regimen; and the patient interface presenting a questionnaire soliciting the patient to answer a plurality of questions, wherein one of the plurality of questions pertains to a current physical condition of the patient or a past physical condition of the patient.

2. The computer-implemented system of claim 1, wherein the regimen is a physical rehabilitation regimen for improving strength or range of motion of the body part.

3. The computer-implemented system of claim 1, wherein the one of the plurality of questions pertains to the current physical condition of the patient.

4. The computer-implemented system of claim 1, wherein the one of the plurality of questions pertains to the past physical condition of the patient.

5. The computer-implemented system of claim 1, wherein the computer-implemented system is configured to take an action in response to a selected response to one of the plurality of questions.

6. The computer-implemented system of claim 5, wherein the action comprises stopping or preventing operation of a treatment apparatus by the patient.

7. The computer-implemented system of claim 5, wherein the action comprises transmitting an alert to a clinician.

8. The computer-implemented system of claim 7, wherein the alert to the clinician comprises an alert message on the clinician interface, the alert message including information relating to the response to the one of the plurality of questions.

9. The computer-implemented system of claim 7, wherein the alert to the clinician comprises a real-time communication to the clinician, and the alert is outside of the clinician interface.

10. The computer-implemented system of claim 5, wherein, before the action is taken, the patient interface presents a prompt for the patient to confirm the particular response to one of the plurality of questions.

11. The computer-implemented system of claim 1, further comprising a server configured to store patient data, the patient data including responses to the plurality of questions.

12. A system for remote treatment, comprising: a clinician interface comprising a patient profile display configured to present status information regarding a patient; a patient interface including an output device and an input device for communicating information, respectively, to and from a patient; and a treatment apparatus configured to be manipulated by the patient, such that the patient can perform a regimen for a body part, the body part comprising at least one of a joint, a bone, or a muscle group; wherein the patient interface and the treatment apparatus are each configured to enable operation from a patient location geographically separate from a location of the clinician interface; and wherein the patient interface presents a questionnaire soliciting a response to a question pertaining to one of a current physical condition of the patient or a past physical condition of the patient.

13. The computer-implemented system of claim 12, wherein the regimen is a physical rehabilitation regimen for improving strength or range of motion of the body part.

14. The computer-implemented system of claim 12, wherein the one of the plurality of questions pertains to the current physical condition of the patient.

15. The computer-implemented system of claim 12, wherein the one of the plurality of questions pertains to the past physical condition of the patient.

16. The system of claim 12, wherein the question is one of a plurality of questions on the questionnaire.

17. The system of claim 12, wherein the question relates to an ability of the patient to use the treatment apparatus.

18. The system of claim 12, wherein the patient interface presents the question in response to occurrence of a triggering event, the triggering event pertaining to the patient's use of the treatment apparatus.

19. The system of claim 12, wherein the treatment apparatus comprises an internal sensor configured to measure at least one of a linear motion or an angular motion of the body part of the patient; and wherein the patient interface presents the question in response to a measurement by the internal sensor.

20. A patient user interface generated by a computer and comprising: a session period action screen presenting real-time status of measurements regarding a patient's use of a treatment apparatus for performing a regimen for a body part, the body part comprising at least one of a joint, a bone, or a muscle group; and a questionnaire soliciting the patient to answer a plurality of questions pertaining to physical conditions of a patient.

21. The computer-implemented system of claim 20, wherein the regimen is a physical rehabilitation regimen for improving strength or range of motion of the body part.

22. The patient user interface of claim 20, wherein the questionnaire comprises a pretreatment questionnaire presenting a plurality of questions; and wherein predetermined responses must be provided before the patient is authorized to use the treatment apparatus.

23. The patient user interface of claim 20, wherein one of the plurality of questions pertains to a current physical condition of the patient.

24. The patient user interface of claim 20, wherein one of the plurality of questions pertains to a past physical condition of the patient.

25. The patient user interface of claim 20, wherein the patient interface presents a help display in response to occurrence of a triggering event, the triggering event pertaining to the patient's use of the treatment apparatus; the help display including a first control for the patient to stop using the treatment apparatus or to request additional help in using the treatment apparatus; and the help display including a second control for the patient to continue using the treatment apparatus.

As will readily be appreciated by a person of ordinary skill of the art in light of having read the present disclosure, as used herein, actions described as being performed in real-time include actions performed in near-real-time without departing from the scope and intent of the present disclosure.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A computer-implemented system for physical rehabilitation of a patient using a treatment apparatus to perform a regimen, the computer-implemented system comprising:
the treatment apparatus, the treatment apparatus including a machine configured to be manipulated by the patient to perform the regimen, the treatment apparatus comprising one or more internal sensors configured to generate data indicating performance of the regimen by the patient;
a clinician interface comprising a patient profile display, the patient profile display configured to present the data and a prompt to modify the regimen based on the data regarding the performance by the patient performing the regimen, wherein the regimen corresponds to a regimen for a body part, the body part comprising at least one of a joint, a bone, or a muscle group; and a patient interface configured to communicate with the treatment apparatus, the patient interface including an output device and an input device for communicating, to and from the patient, information regarding the performance of the regimen implemented by using the treatment apparatus, the patient interface presenting instructions and status information to the patient regarding the performance of the regimen, the patient interface presenting a questionnaire soliciting the patient to answer a plurality of questions, wherein one of the plurality of questions pertains to a current physical condition of the patient or a past physical condition of the patient, and wherein, responsive to at least one of the clinician interface and the patient interface and in response to the answer to the one of the plurality questions, the treatment apparatus selectively stops or prevents operation of the machine by the patient.

2. The computer-implemented system of claim 1, wherein the regimen is a physical rehabilitation regimen for improving strength or range of motion of the body part.

3. The computer-implemented system of claim 1, wherein the one of the plurality of questions pertains to the current physical condition of the patient.

4. The computer-implemented system of claim 1, wherein the one of the plurality of questions pertains to the past physical condition of the patient.

5. The computer-implemented system of claim 1, wherein the computer-implemented system is configured to take an action in response to a selected response to one of the plurality of questions.

6. The computer-implemented system of claim 5, wherein the action comprises transmitting an alert to a clinician.

7. The computer-implemented system of claim 6, wherein the alert to the clinician comprises an alert message on the clinician interface, the alert message including information relating to the response to the one of the plurality of questions.

8. The computer-implemented system of claim 6, wherein the alert to the clinician comprises a real-time communication to the clinician, and the alert is outside of the clinician interface.

9. The computer-implemented system of claim 5, wherein, before the action is taken, the patient interface presents a prompt for the patient to confirm response to one of the plurality of questions.

10. The computer-implemented system of claim 1, further comprising a server configured to store patient data, the patient data including responses to the plurality of questions.

11. A system for remote treatment of a patient using a treatment apparatus, the system comprising:

a clinician interface comprising a patient profile display configured to present status information regarding the patient;

a patient interface configured to communicate with the treatment apparatus, the patient interface including an output device and an input device for communicating information, respectively, to and from the patient, the information being indicative of performance of a regimen by the patient while using the treatment apparatus; and the treatment apparatus, the treatment apparatus including a machine configured to be manipulated by the patient, such that the patient can perform the regimen for a body part, the body part comprising at least one of a joint, a bone, or a muscle group, the treatment apparatus comprising one or more internal sensors that produce data regarding the performance of the regimen, wherein the patient interface and the treatment apparatus are each configured to enable operation from a patient location geographically separate from a location of the clinician interface, wherein the patient interface presents a questionnaire soliciting an answer to a question pertaining to one of a current physical condition of the patient or a past physical condition of the patient, wherein the clinician interface presents a prompt to modify the regimen based on the data regarding the performance of the regimen, and wherein, responsive to at least one of the clinician interface and the patient interface and in response to the answer to the question, the treatment apparatus selectively stops or prevents operation of the machine by the patient.

12. The system of claim 11, wherein the regimen is a physical rehabilitation regimen for improving strength or range of motion of the body part.

13. The system of claim 11, wherein the question pertains to the current physical condition of the patient.

14. The system of claim 11, wherein the question pertains to the past physical condition of the patient.

15. The system of claim 11, wherein the question is one of a plurality of questions on the questionnaire.

16. The system of claim 11, wherein the question relates to an ability of the patient to use the treatment apparatus.

17. The system of claim 11, wherein the patient interface presents the question in response to occurrence of a triggering event, the triggering event pertaining to the patient's use of the treatment apparatus.

18. The system of claim 11, wherein the treatment apparatus comprises an internal sensor configured to measure at least one of a linear motion or an angular motion of the body part of the patient; and wherein the patient interface presents the question in response to a measurement by the internal sensor.

19. A patient user interface configured to communicate with a treatment apparatus, the patient user interface being generated by a computer and comprising:

a session period action screen, generated by the computer, presenting real-time status of measurements regarding a patient's use of a-the treatment apparatus for performing a regimen for a body part while the treatment apparatus is being used by the patient to perform the regimen, the body part comprising at least one of a joint, a bone, or a muscle group, wherein the treatment apparatus includes a machine configured to be manipulated by the patient performing the regimen, the treatment apparatus comprising one or more internal sensors that produce the measurements regarding the patient's use of the treatment apparatus; and a questionnaire soliciting the patient to answer a plurality of questions pertaining to physical conditions of the patient, wherein the patient user interface generates a triggering event based on the measurements, the patient user interface presents a help display in response to the triggering event, and responsive to the patient user interface and in response to an answer to one of the plurality questions, the treatment apparatus selectively stops or prevents operation of the machine by the patient.

20. The patient user interface of claim 19, wherein the regimen is a physical rehabilitation regimen for improving strength or range of motion of the body part.

21. The patient user interface of claim 19, wherein the questionnaire comprises a pretreatment questionnaire presenting the plurality of questions, and wherein predetermined responses must be provided before the patient is authorized to use the treatment apparatus.

22. The patient user interface of claim 19, wherein one of the plurality of questions pertains to a current physical condition of the patient.

23. The patient user interface of claim 19, wherein one of the plurality of questions pertains to a past physical condition of the patient.

24. The patient user interface of claim 19, wherein the help display includes a first control for the patient to stop using the treatment apparatus or to request additional help in using the treatment apparatus; and the help display includes a second control for the patient to continue using the treatment apparatus.

* * * * *